(12) United States Patent
Irisawa et al.

(10) Patent No.: US 8,378,703 B2
(45) Date of Patent: Feb. 19, 2013

(54) CONTAINER, A METHOD FOR DISPOSING THE SAME, AND A MEASUREMENT METHOD

(75) Inventors: Akiyoshi Irisawa, Miyagi (JP); Shigeki Nishina, Miyagi (JP)

(73) Assignee: Advantest Corporation, Tokyo (JP)

( * ) Notice: Subject to any disclaimer, the term of this patent is extended or adjusted under 35 U.S.C. 154(b) by 701 days.

(21) Appl. No.: 12/486,178

(22) Filed: Jun. 17, 2009

(65) Prior Publication Data

US 2010/0271056 A1 Oct. 28, 2010

(30) Foreign Application Priority Data

Apr. 23, 2009 (JP) ................................. 2009-104699

(51) Int. Cl.
*G01R 31/308* (2006.01)
*G01R 31/302* (2006.01)
(52) U.S. Cl. ............................... 324/754.23; 324/754.29
(58) Field of Classification Search ........................ None
See application file for complete search history.

(56) References Cited

U.S. PATENT DOCUMENTS

| 6,798,521 | B2 * | 9/2004 | Elkind et al. ................. 356/445 |
| 7,119,339 | B2 | 10/2006 | Ferguson et al. |
| 7,808,636 | B2 * | 10/2010 | Schulkin et al. .............. 356/365 |
| 8,294,121 | B2 * | 10/2012 | Naitoh ..................... 250/453.11 |
| 2003/0110809 | A1 | 6/2003 | Linder et al. |
| 2004/0095147 | A1 | 5/2004 | Cole |
| 2006/0146334 | A1 | 7/2006 | Cluff et al. |
| 2006/0268945 | A1 | 11/2006 | Minamide et al. |
| 2007/0257216 | A1 | 11/2007 | Withers et al. |
| 2009/0128803 | A1 * | 5/2009 | Gan ............................. 356/129 |

FOREIGN PATENT DOCUMENTS

| EP | 1621902 | 2/2006 |
| GB | 2405466 | 3/2005 |
| JP | 1-195346 | 8/1989 |
| JP | 10-332577 | 12/1998 |
| JP | 2000-121550 | 4/2000 |
| JP | 2002-139422 | 5/2002 |
| JP | 2005-507999 | 3/2005 |

(Continued)

OTHER PUBLICATIONS

Ferguson et al., "T-ray computed tomography", Optics Letters, vol. 27, No. 15, pp. 1312-1314, Aug. 1, 2002.

(Continued)

*Primary Examiner* — Richard Isla Rodas
(74) *Attorney, Agent, or Firm* — Greenblum & Bernstein, P.L.C.

(57) ABSTRACT

The present invention restrains adverse effects caused by refraction of a terahertz wave by a device under test when the terahertz wave is fed to the device under test for measurement. A container 10 contains at least part of a device under test 1 to be measured by a terahertz wave measurement device. The container 10 includes a gap portion 11 that internally arranges at least a part of the device under test 1, and an enclosure portion 12 that includes a first curved surface portion S1, and a second curved surface portion S2, and arranges the gap portion 11 between the first curved surface portion S1 and the second curved surface portion S2, thereby enclosing the gap portion 11. Moreover, a relationship $n1<n2$ holds where $n2$ is the refractive index of the enclosure portion, and $n1$ is the refractive index of the device under test. Further, both the first curved surface portion S1 and the second curved surface portion S2 are convex surfaces.

11 Claims, 21 Drawing Sheets

FOREIGN PATENT DOCUMENTS

WO 03/038373 5/2003

OTHER PUBLICATIONS

Naoki Sunaguchi et al., "THz-wave tomographic imaging from limited projections," The 51th Japan Joint Automatic Control Conference, Nov. 2008, pp. 154-157, Nov. 22, 2008.

S. Wang et a., "Pulsed terahertz tomography", J. Phys. D, vol. 37 (2004), R1-R36.

Roman C et al., "Terahertz dielectric characterisation of polymethacrylimide rigid foam: The perfect sheer plate?", Electronics Letters, IEE Stevenage, GB, vol. 40, No. 19, XP006022653, Sep. 16, 2004, pp. 1167-1169.

Kato E et al., "3D Spectroscopic computed tomography imaging using terahertz waves", Infrared Millimeter and Terahertz Waves (IRMMW-THZ), 2010 35TH International Conference on, IEEE, Piscataway, NJ, USA, XP031783233, Sep. 5, 2010, pp. 1-2.

Abraham E et al., "Refraction losses in terahertz computed tomography", Optics Communications, North-Holland Publishing Co. Amsterdam, NL, vol. 283, No. 10, XP02696340, May 15, 2010, pp. 2050-2055.

Search report from E.P.O., mail date is Nov. 26, 2012.

\* cited by examiner $n1 > n2$ $\theta_A > \theta_B$ (a)

$n1 < n2a$
$n1 > n2b$ (b)

$n1 > n2a$
$n1 < n2b$ $n1<n2a$
$n1<n2b$

CONTAINER, A METHOD FOR DISPOSING THE SAME, AND A MEASUREMENT METHOD

BACKGROUND ART

1. Field of the Invention

The present invention relates to tomography using an electromagnetic wave (frequency thereof is equal to or more than 0.01 [THz], and equal to or less than 100 [THz]) (such as a terahertz wave (frequency thereof is equal to or more than 0.03 [THz], and equal to or less than 10 [THz]), for example).

2. Description of the Prior Art

There has conventionally been the computed tomography (CT) as a method for obtaining tomographic information on a device under test. This method carried out while a generator and a detector of the X ray are used is referred to as X-ray CT. With the X-ray CT, it is possible to acquire tomographic information on a human body in non-destructive and non-contact manner.

SUMMARY OF THE INVENTION

However, it is difficult for the X-ray CT to detect internal states (such as defects and distortions) of industrial products constructed by semiconductors, plastics, ceramics, woods, and papers (hereinafter referred to as "raw materials"). This is because the X-ray presents a high transmission property to any materials.

On the other hand, the terahertz wave properly transmits through the raw materials of the industrial products described above. Therefore, the CT carried out while a generator and a detector of the terahertz wave (hereinafter referred to as "terahertz wave CT") are used can detect internal states of the industrial products. Patent Document 1 and Non-Patent Document 1 describe the terahertz wave CT.

(Patent Document 1) U.S. Pat. No. 7,119,339
(Non-Patent Document 1) S. Wang et al., "Pulsed terahertz tomography," J. Phys. D, Vol. 37 (2004), R1-R36

However, according to the terahertz wave CT, when the terahertz wave is obliquely made incident to or emitted from a device under test, the terahertz wave is refracted, and thus does not travel straight. On this occasion, it is assumed that the refraction index of the ambient air of the device under test is 1, and the refraction index of the device under test for the terahertz wave CT is more than 1.

FIG. 21 shows estimated optical paths of the terahertz wave when the refraction index of a conventional device under test is 1.4, and the refraction index of the ambient air of the device under test is 1. Referring to FIG. 21, it is appreciated that a terahertz wave made incident from the left of the device under test (DUT) is refracted by the DUT.

Due to the fact that the terahertz wave does not travel straight, the terahertz wave cannot reach a detector, and an image of the DUT cannot thus be obtained at a sufficient sensitivity.

Moreover, due to the fact that the terahertz wave does not travel straight, a detected terahertz wave may not have traveled straight through the DUT before the arrival. Therefore, when an image of the DUT is obtained from the detected terahertz wave, artifacts such as obstructive shadows and pseudo images may appear on the image.

Thus, it is an object of the present invention, when an electromagnetic wave (frequency thereof is equal to or more than 0.01 [THz] and equal to or less than 100 [THz]) including the terahertz wave is fed to a DUT for measurement, to restrain adverse effects caused by refraction of the electromagnetic wave including the terahertz wave by the DUT.

According to the present invention, a container for containing at least a part of a device under test to be measured by an electromagnetic wave measurement device, includes: a gap portion that internally disposes at least a part of the device under test; and an enclosure portion that includes a first curved surface portion and a second curved surface portion, and disposes the gap portion between the first curved surface portion and the second curved surface portion, thereby enclosing the gap portion, wherein: the refractive index n2 of the enclosure portion is larger than the refractive index n1 of the device under test; both the first curved surface and the second curved surface are convex surfaces; and the electromagnetic wave measurement device outputs an electromagnetic wave at a frequency equal to or more than 0.01 [THz] and equal to or less than 100 [THz] toward the device under test.

According to the thus constructed container for containing at least a part of a device under test to be measured by an electromagnetic wave measurement device, a gap portion internally disposes at least a part of the device under test. An enclosure portion includes a first curved surface portion and a second curved surface portion, and disposes the gap portion between the first curved surface portion and the second curved surface portion, thereby enclosing the gap portion. The refractive index n2 of the enclosure portion is larger than the refractive index n1 of the device under test, and both the first curved surface and the second curved surface are convex surfaces. The electromagnetic wave measurement device outputs an electromagnetic wave at a frequency equal to or more than 0.01 [THz] and equal to or less than 100 [THz] toward the device under test.

According to the present invention, a container for containing at least a part of a device under test to be measured by an electromagnetic wave measurement device, includes: a gap portion that internally disposes at least a part of the device under test; and an enclosure portion that includes a first curved surface portion and a second curved surface portion, and disposes the gap portion between the first curved surface portion and the second curved surface portion, thereby enclosing the gap portion, wherein: the refractive index n2 of the enclosure portion is smaller than the refractive index n1 of the device under test; both the first curved surface and the second curved surface are concave surfaces; and the electromagnetic wave measurement device outputs an electromagnetic wave at a frequency equal to or more than 0.01 [THz] and equal to or less than 100 [THz] toward the device under test.

According to the thus constructed container for containing at least a part of a device under test to be measured by an electromagnetic wave measurement device, a gap portion internally disposes at least a part of the device under test. An enclosure portion includes a first curved surface portion and a second curved surface portion, and disposes the gap portion between the first curved surface portion and the second curved surface portion, thereby enclosing the gap portion. The refractive index n2 of the enclosure portion is smaller than the refractive index n1 of the device under test, and both the first curved surface and the second curved surface are concave surfaces. The electromagnetic wave measurement device outputs an electromagnetic wave at a frequency equal to or more than 0.01 [THz] and equal to or less than 100 [THz] toward the device under test.

According to the container of the present invention, a contour of a plane shape of the gap portion may include an arc.

According to the container of the present invention, a radius of a contour of a plane cross section of the gap portion may change according to the height of the gap portion.

According to the container of the present invention, the enclosure portion can be divided along a separation surface; and the separation surface may intersect with the gap portion.

According to the present invention, the container may include an insertion member that is inserted in a space between the device under test and the gap portion, wherein: a contour of a plane shape of an integrated body of the device under test and the insertion member is concentric with a contour of a plane shape of the gap portion; and a relationship of $n1-0.1 \leq n3 \leq n1+0.1$ holds where n3 is the refraction index of the insertion member, and n1 is the refraction index of the device under test.

According to the container of the present invention, a distance between the contour of the plane shape of the integrated body of the device under test and the insertion member and the contour of the plane shape of the gap portion may be equal to or less than a quarter of the wavelength of the electromagnetic wave output from the electromagnetic wave measurement device toward the device under test.

According to the present invention, the container may includes a filling material which is filled in a space between the device under test and the gap portion, wherein a relationship of $n1-0.1 \leq n4 \leq n1+0.1$ holds where n4 is the refraction index of the filling material, and n1 is the refraction index of the device under test.

According to the container of the present invention, a distance between a contour of a plane shape of the device under test and the contour of the plane shape of the gap portion may be equal to or less than a quarter of the wavelength of the electromagnetic wave output from the electromagnetic wave measurement device toward the device under test.

According to the present invention, a container for containing at least a part of a device under test to be measured by an electromagnetic wave measurement device, includes: a first cover portion that includes a first curved surface portion which receives an electromagnetic wave output from the electromagnetic wave measurement device toward the device under test, and a first concave portion which is closer to the device under test than the first curved surface portion, and through which the electromagnetic wave transmits, and has a refraction index of n2a; and a second cover portion that includes a second concave portion which receives the electromagnetic wave which has transmitted through the device under test, and a second curved surface portion which is farther than the second concave portion from the device under test, and through which the electromagnetic wave transmits, and has a refraction index of n2b, wherein: if n2a is larger than the refraction index n1 of the device under test, the first curved surface portion is a convex surface; if n2a is smaller than n1, the first curved surface portion is a concave surface; if n2b is larger than n1, the second curved surface portion is a convex surface; if n2b is smaller than n1, the second curved surface portion is a concave surface; and the electromagnetic wave measurement device outputs the electromagnetic wave at a frequency equal to or more than 0.01 [THz] and equal to or less than 100 [THz] toward the device under test.

According to the thus constructed container for containing at least a part of a device under test to be measured by an electromagnetic wave measurement device, a first cover portion includes a first curved surface portion which receives an electromagnetic wave output from the electromagnetic wave measurement device toward the device under test, and a first concave portion which is closer to the device under test than the first curved surface portion, and through which the electromagnetic wave transmits, and has a refraction index of n2a. A second cover portion includes a second concave portion which receives the electromagnetic wave which has transmitted through the device under test, and a second curved surface portion which is farther than the second concave portion from the device under test, and through which the electromagnetic wave transmits, and has a refraction index of n2b. If n2a is larger than the refraction index n1 of the device under test, the first curved surface portion is a convex surface; if n2a is smaller than n1, the first curved surface portion is a concave surface; if n2b is larger than n1, the second curved surface portion is a convex surface; and if n2b is smaller than n1, the second curved surface portion is a concave surface. The electromagnetic wave measurement device outputs the electromagnetic wave at a frequency equal to or more than 0.01 [THz] and equal to or less than 100 [THz] toward the device under test.

According to the container of the present invention, n2a and n2b may be different from each other.

According to the container of the present invention, the curvature radius of a plane shape of the first curved surface portion and the curvature radius of a plane shape of the second curved surface portion may be different from each other.

According to the container of the present invention, contours of plane shapes of the first concave portion and the second concave portion may include an arc.

According to the container of the present invention, radii of contours of plane cross sections of the first concave portion and the second concave portion may change respectively according to the heights of the first concave portion and the second concave portion.

According to the present invention, the container may includes an insertion member that is inserted in a space between the device under test, and the first concave portion and the second concave portion, wherein: a contour of an integrated body of the device under test and the insertion member is concentric with contours of plane shapes of the first concave portion and the second concave portion; and a relationship of $n1-0.1 \leq n3 \leq n1+0.1$ holds where n3 is the refraction index of the insertion member, and n1 is the refraction index of the device under test.

According to the container of the present invention, distances between a contour of a plane shape of the integrated body of the device under test and the insertion member and the contours of the plane shapes of the first concave portion and the second concave portion may be equal to or less than a quarter of the wavelength of the electromagnetic wave output from the electromagnetic wave measurement device toward the device under test.

According to the present invention, the container may include a filling material which is filled in a space between the device under test, and the first concave portion and the second concave portion, wherein a relationship of $n1-0.1 \leq n4 \leq n1+0.1$ holds where n4 is the refraction index of the filling material, and n1 is the refraction index of the device under test.

According to the container of the present invention, distances between a contour of a plane shape of the device under test and the contours of the plane shapes of the first concave portion and the second concave portion may be equal to or less than a quarter of the wavelength of the electromagnetic wave output from the electromagnetic wave measurement device toward the device under test.

According to the container of the present invention, the first curved surface portion and the second curved surface portion may be cylindrical surfaces.

According to the container of the present invention, both of or either of the first curved surface portion and the second curved surface portion may be a non-cylindrical surface.

According to the present invention, a container arrangement method for arranging the container of the present invention containing the device under test for measuring the device under test by the electromagnetic wave measurement device, includes a step of arranging the container so that an optical axis of the first curved surface portion is parallel with a traveling direction of the electromagnetic wave output from the electromagnetic wave measurement device toward the device under test.

According to the present invention, a container arrangement method for arranging the container of the present invention containing the device under test for measuring the device under test by the electromagnetic wave measurement device, includes a step of arranging the container such that an optical axis of the first curved surface portion intersects with the traveling direction of the electromagnetic wave output from the electromagnetic wave measurement device toward the device under test at an angle of more than 0 degree and less than 90 degree.

According to the present invention, a method for measuring the device under test contained in the container of the present invention using the electromagnetic wave measurement device, includes: an output step of outputting the electromagnetic wave by the electromagnetic wave measurement device; and a detection step of detecting the electromagnetic wave which has transmitted through the device under test by the electromagnetic wave measurement device, wherein the container and the device under test move horizontally with respect to an optical path of the electromagnetic wave while the output step and the detection step are being carried out.

According to the present invention, a method for measuring the device under test contained in the container of the present invention using the electromagnetic wave measurement device, includes: an output step of outputting the electromagnetic wave by the electromagnetic wave measurement device; and a detection step of detecting the electromagnetic wave which has transmitted through the device under test by the electromagnetic wave measurement device, wherein an optical path of the electromagnetic wave moves horizontally with respect to the container while the output step and the detection step are being carried out.

According to the present invention, a method for measuring the device under test contained in the container of the present invention using the electromagnetic wave measurement device, includes: an output step of outputting the electromagnetic wave by the electromagnetic wave measurement device; and a detection step of detecting the electromagnetic wave which has transmitted through the device under test by the electromagnetic wave measurement device, wherein the device under test rotates about a line extending vertically as an axis of rotation while the output step and the detection step are being carried out.

According to the present invention, a method for measuring the device under test contained in the container of the present invention using the electromagnetic wave measurement device, includes: an output step of outputting the electromagnetic wave by the electromagnetic wave measurement device; and a detection step of detecting the electromagnetic wave which has transmitted through the device under test by the electromagnetic wave measurement device, wherein the container and an optical path of the electromagnetic wave rotate about a line extending vertically as an axis of rotation while the output step and the detection step are being carried out.

According to the present invention, a method for measuring the device under test contained in the container of the present invention using the electromagnetic wave measurement device, includes: an output step of outputting the electromagnetic wave by the electromagnetic wave measurement device; and a detection step of detecting the electromagnetic wave which has transmitted through the device under test by the electromagnetic wave measurement device, wherein the container and an optical path of the electromagnetic wave move vertically with respect to the device under test while the output step and the detection step are being carried out.

According to the present invention, a method for measuring the device under test contained in the container of the present invention using the electromagnetic wave measurement device, includes: an output step of outputting the electromagnetic wave by the electromagnetic wave measurement device; and a detection step of detecting the electromagnetic wave which has transmitted through the device under test by the electromagnetic wave measurement device, wherein the container and the device under test move vertically with respect to an optical path of the electromagnetic wave while the output step and the detection step are being carried out.

According to the present invention, a method for measuring the device under test contained in the container of the present invention using the electromagnetic wave measurement device, includes: an output step of outputting the electromagnetic wave by the electromagnetic wave measurement device; and a detection step of detecting the electromagnetic wave which has transmitted through the device under test by the electromagnetic wave measurement device, wherein the device under test moves vertically with respect to the container and an optical path of the electromagnetic wave while the output step and the detection step are being carried out.

According to the present invention, a method for measuring the device under test contained in the container of the present invention using the electromagnetic wave measurement device, includes: an output step of outputting the electromagnetic wave by the electromagnetic wave measurement device; and a detection step of detecting the electromagnetic wave which has transmitted through the device under test by the electromagnetic wave measurement device, wherein an optical path of the electromagnetic wave moves vertically with respect to the container and the device under test while the output step and the detection step are being carried out.

BEST MODE FOR CARRYING OUT THE INVENTION

A description will now be given of embodiments of the present invention with reference to drawings.

First Embodiment

Figure 1:
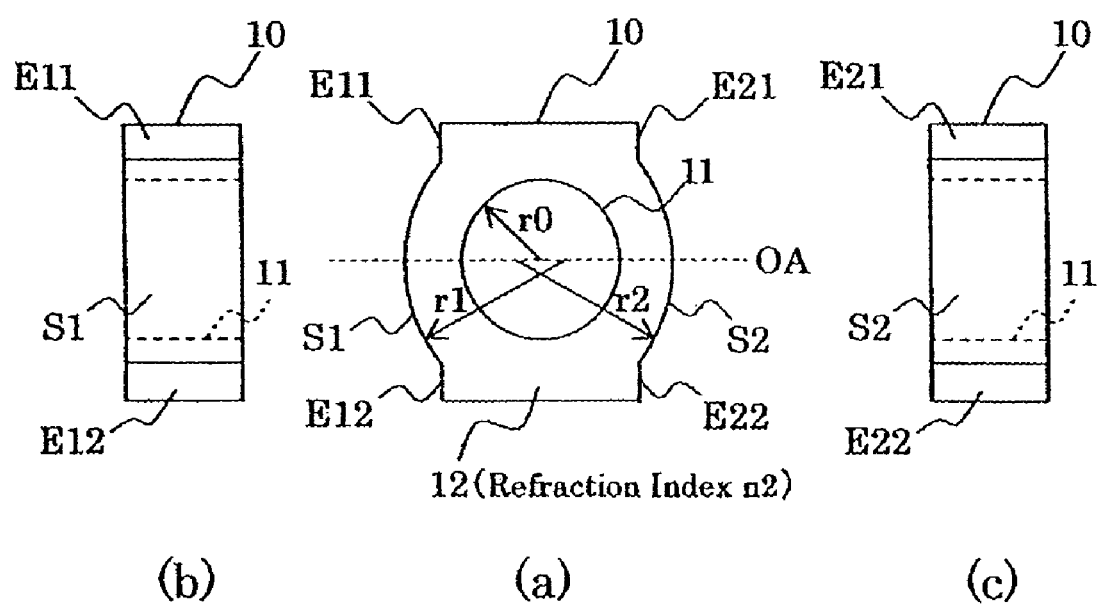
FIG. 1(a) is a plan view of a container 10 according to the first embodiment of the present invention.
FIG. 1(b) is a left side view of the container 10.
FIG. 1(c) is a right side view of the container 10.
Figure 2:
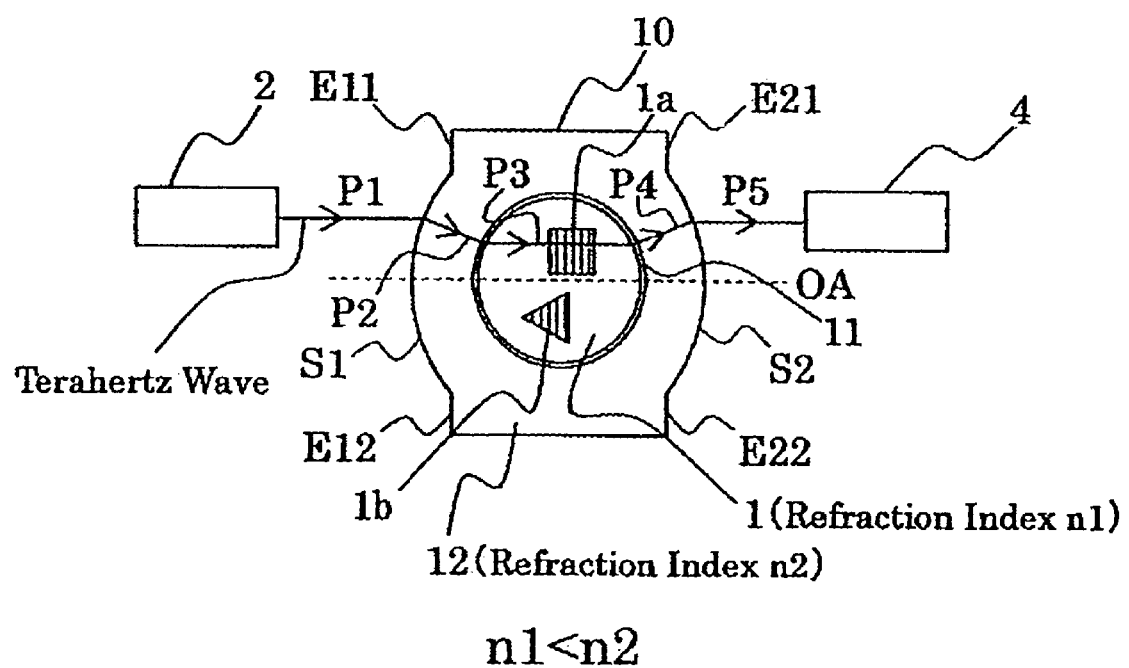
FIG. 2 is a plan view in a state in which at least a part of a device under test (DUT) 1 is stored in the container 10 according to the first embodiment of the present invention, and a terahertz wave is irradiated on the container 10.

FIG. 1(a) is a plan view of a container 10 according to the first embodiment of the present invention, FIG. 1(b) is a left side view of the container 10, and FIG. 1(c) is a right side view of the container 10. FIG. 2 is a plan view in a state in which at least a part of a device under test (DUT) 1 is stored in the container 10 according to the first embodiment of the present invention, and a terahertz wave is irradiated on the container 10.

Referring to FIG. 2, a terahertz wave measurement device (electromagnetic wave measurement device) includes a terahertz wave output device 2 and a terahertz wave detector 4. The terahertz wave output device 2 outputs the terahertz wave toward the DUT 1. The terahertz wave detector 4 detects the terahertz wave which has transmitted through the DUT 1 and the container 10.

It should be noted that the terahertz wave measurement device (electromagnetic wave measurement device) employs, as an electromagnetic wave to be output and to be detected, the terahertz wave (the frequency thereof is equal to or more than 0.03 [THz] and equal to or less than 10 [THz], for example). However, the electromagnetic wave to be output and detected by the terahertz wave measurement device (electromagnetic wave measurement device) is not limited to the terahertz wave, and may be an electromagnetic wave the frequency of which is equal to or more than 0.01 [THz] and equal to or less than 100 [THz].

Figure 16:
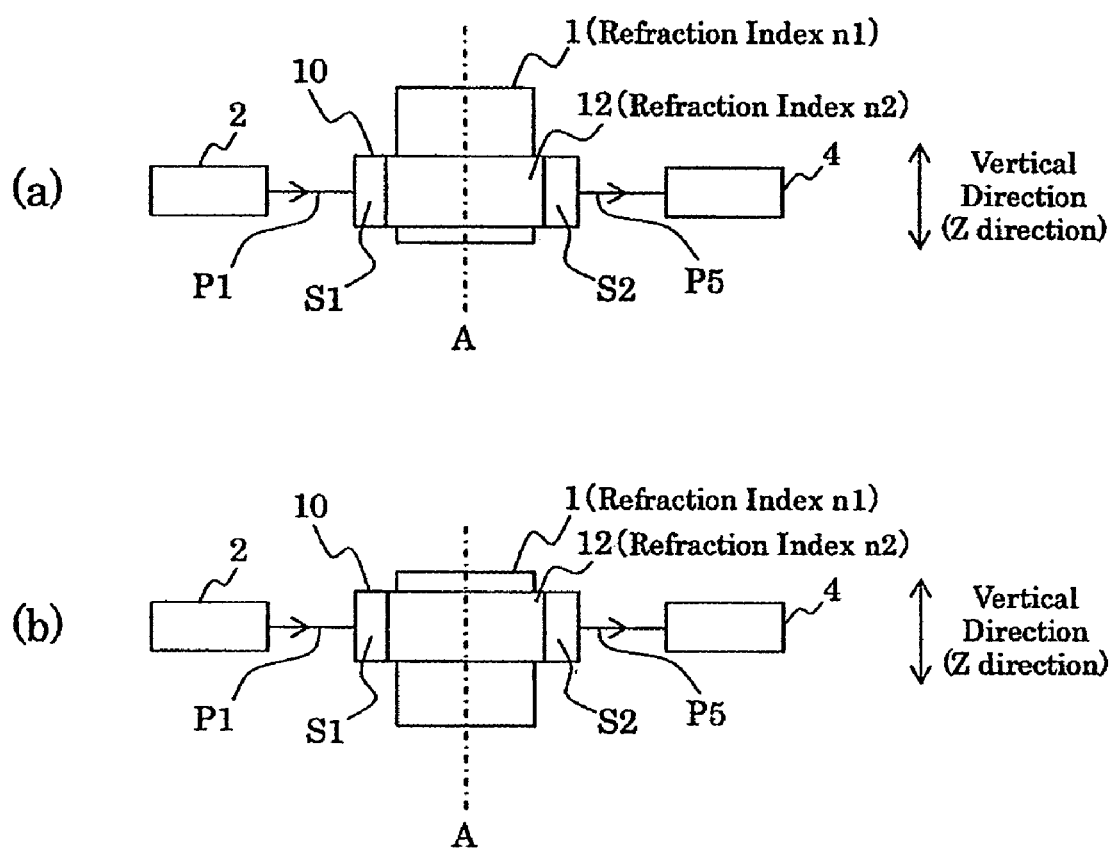
FIGS. 16(a) and 16(b) are front views of the container 10 and the terahertz wave measurement device according to the thirteenth embodiment.
Figure 17:
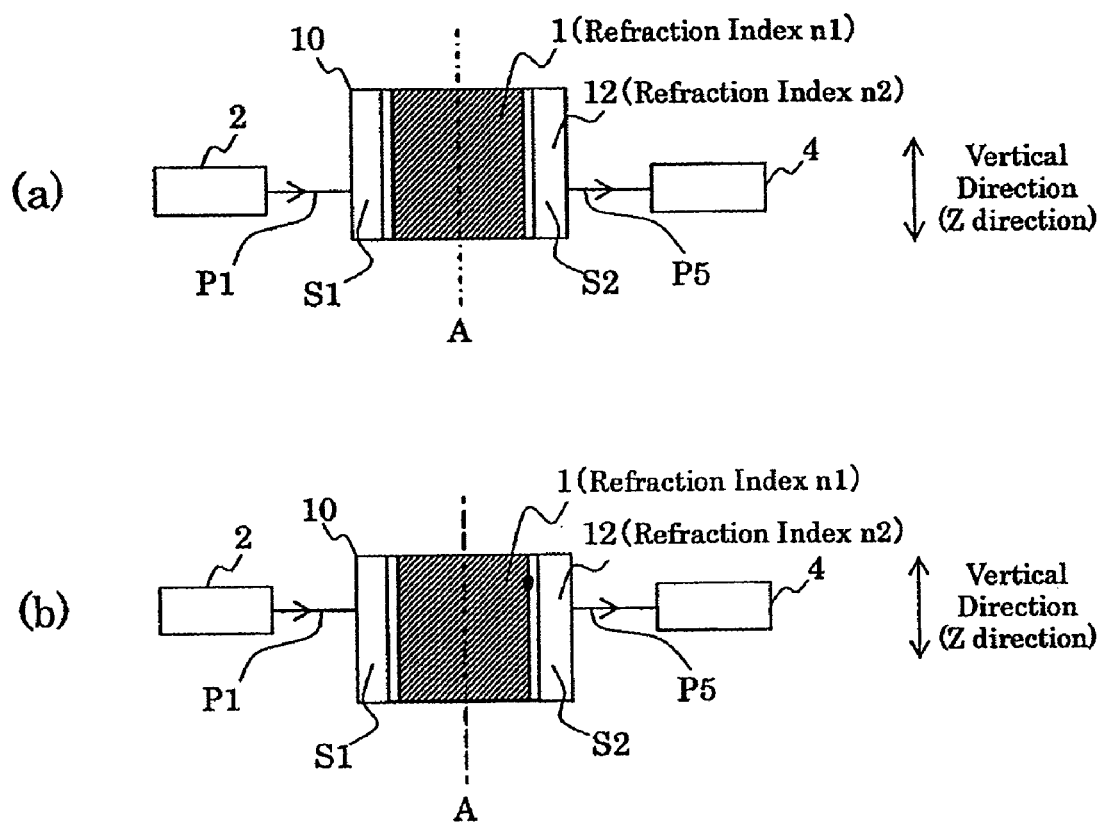
FIGS. 17(a) and 17(b) are front views of the container 10 and the terahertz wave measurement device according to the fourteenth embodiment.

The container 10 stores at least a part of the DUT 1 to be measured by the terahertz wave measurement device. It should be noted that the container 10 may store the DUT 1 partially (refer to FIGS. 16(a) and 16(b)) or entirely (refer to FIGS. 17(a) and 17(b)).

The container 10 includes a gap portion 11 and an enclosure portion 12. The gap portion 11 is a circular gap with a radius of r0 viewed from above (refer to FIGS. 1(a) to 1(c)). At least a part of the DUT 1 is disposed inside the gap portion 11 (refer to FIG. 2).

The enclosure portion 12 includes a first curved surface portion S1 and a second curved surface portion S2. The first curved surface portion S1 is a cylindrical surface with a radius of r1 (a part of a side surface of a cylinder the bottom surface of which is a circle with the radius of r1). The second curved surface portion S2 is a cylindrical surface with a radius of r2 (a part of a side surface of a cylinder the bottom surface of which is a circle with the radius of r2). It should be noted that the gap portion 11 is represented as a circle with the radius of r0, the first curved surface portion S1 is represented as an arc with the radius of r1 (>r0), and the second curved surface portion S2 is represented as an arc with the radius of r2 (=r1) in the plan view (FIG. 1(a)). All the centers of the circle and the arcs are present on an optical axis OA of the container 10. The center of the arc representing the first curved surface portion S1 and the center of the arc representing the second curved surface portion S2 are point symmetrical, and the center of the symmetry is the center of the circle representing the gap portion 11 in the plan view (FIG. 1(a)). Moreover, the arc representing the first curved surface portion S1 and the arc representing the second curved surface portion S2 are line symmetrical.

Though there has been given a description that the first curved surface portion S1 and the second curved surface portion S2 are the cylindrical surfaces, both or either of the first curved surface portion S1 and the second curved surface portion S2 may be non-cylindrical surface. This holds true for the other embodiments.

The gap portion 11 is arranged between the first curved surface portion S1 and the second curved surface portion S2. The enclosure portion 12 encloses the gap portion 11. On this occasion, the refraction index of the DUT 1 is n1, and the refraction index of the enclosure portion 12 is n2. Then, n1<n2 holds. Moreover, both the first curved surface portion S1 and the second curved surface portion S2 are convex surfaces. Further, n1 and n2 may not be equal to the refraction index (such as 1) of the atmosphere of the container 10.

It should be noted that the material of the enclosure portion 12 may be a resin material such as Teflon (registered trademark), polyethylene, and the like. These resin materials cannot usually be used for measurement of a light ray in the visible light area or the infrared light area. However, these resin materials present a little absorption and scatter of the light ray of the terahertz wave, and can thus be used for measurement by means of the terahertz wave.

Figure 3:
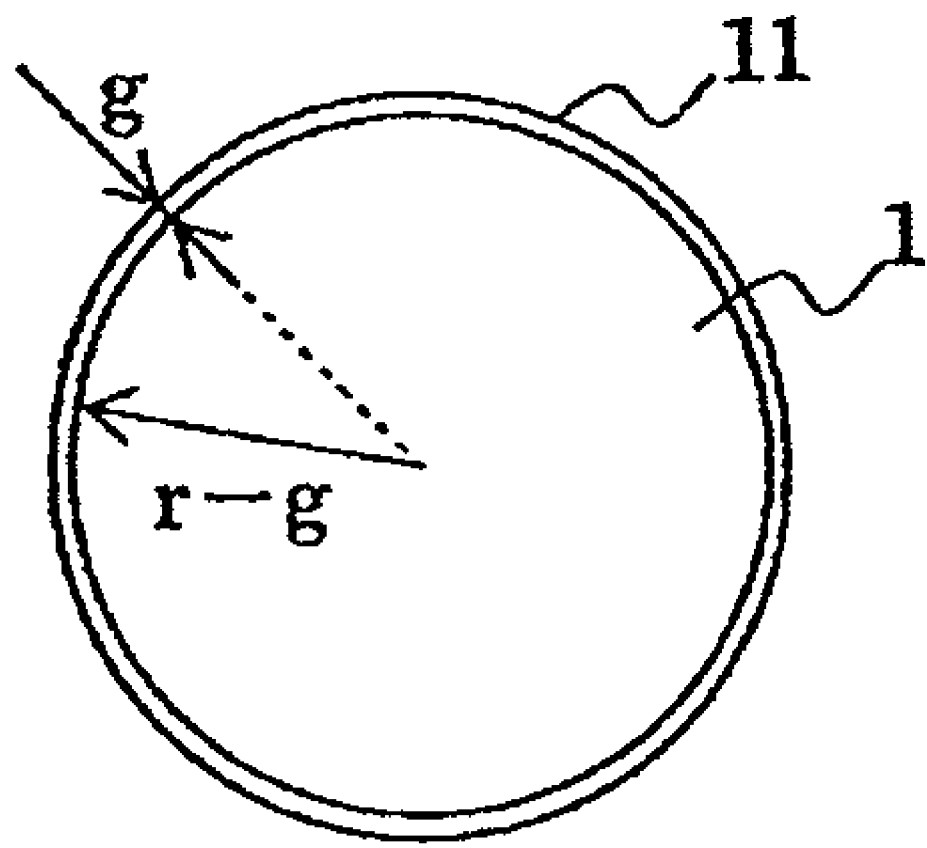
FIG. 3 is an enlarged plan view of the DUT 1 and the gap portion 11 when at least a part of the DUT 1 is stored in the container 10.

FIG. 3 is an enlarged plan view of the DUT 1 and the gap portion 11 when at least a part of the DUT 1 is stored in the container 10. The distance between a contour of a plane shape (shape viewed from above and a plane cross section) of the DUT 1 and a contour of a plane shape of the gap portion 11 (shape viewed from above and a plane cross section) is g. Then, the plane shape of the DUT 1 is a circle with a radius of r-g. Thus, the DUT 1 is a cylinder with a bottom surface of a circle with a radius of r-g.

It is preferable that g$\leq$λ/4. It should be noted that λ is the wavelength of the terahertz wave output from the terahertz wave output device 2 of the terahertz wave measurement device toward the DUT 1. When g$\leq$λ/4, it is possible to restrain an air layer in the gap between the contour of the DUT 1 and the contour of the plane shape of the gap portion 11 from reflecting the terahertz wave. The reflection of the terahertz wave leads to a loss of the terahertz wave, and the setting of g$\leq$λ/4 leads to the restraint of the loss of the terahertz wave.

It should be noted that, referring to FIG. 2, the optical axis OA of the first curved surface portion S1 is set so that it is parallel with the traveling direction (optical path P1) of the terahertz wave output from the terahertz wave output device 2 of the terahertz wave measurement device toward the DUT 1. The container 10 is provided so as to measure the DUT 1 by the terahertz wave measurement device.

Moreover, the enclosure portion 12 includes end planes E11 and E12 (on the side of the first curved surface portion S1) and end planes E21 and E22 (on the side of the second curved surface portion S2) on end portions (top and bottom in FIG. 1(a)). The end planes E11 and E12 and the end planes E21 and E22 are parallel with each other, and are orthogonal to the optical axis OA. Thus, even when the terahertz wave traveling on the light path P1 parallel with the optical axis OA is made incident to the end plane E11 (or E12), the terahertz wave simply travels straight in the enclosure portion 12 (is not made incident to the DUT 1), and is emitted from the end plane E21 (or E22).

A description will now be given of an operation of the first embodiment.

Referring to FIG. 2, the terahertz wave output device 2 of the terahertz wave measurement device outputs the terahertz wave. The terahertz wave output from the terahertz output device 2 (optical path P1) is irradiated on the first curved surface portion S1. Then, the terahertz wave is refracted, and travels on the optical path P2 in the enclosure portion 12. On this occasion, the thickness of the air layer between the contour of the DUT 1 and the contour of the plane shape of the gap portion 11 is negligible since the thickness is small. The terahertz wave which has traveled on the optical path P2 is made incident to the DUT 1, is refracted, and travels on the optical path P3 inside the DUT 1. It should be noted that the light path P3 is approximately parallel with the light path P1 and the optical axis OA.

Figure 4:
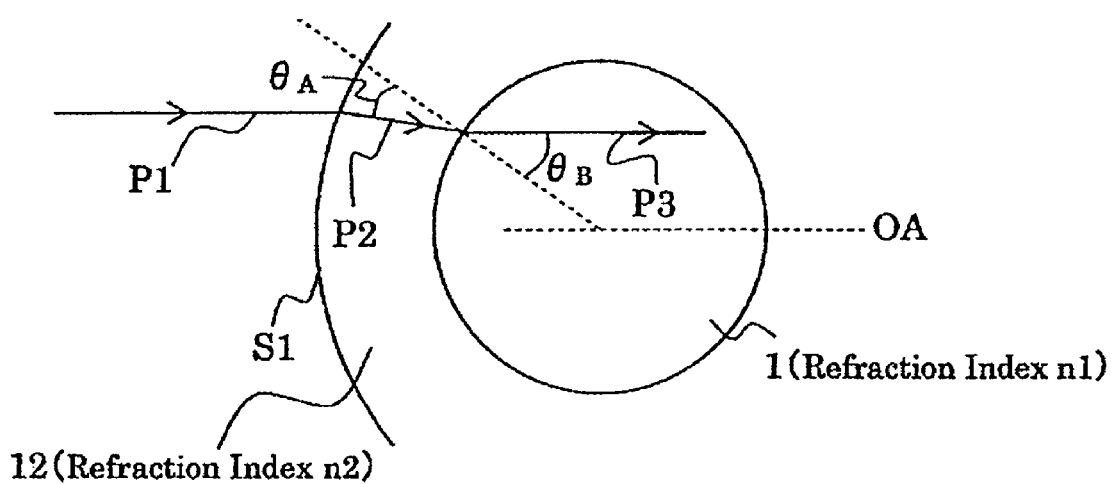
FIG. 4 is a plan view of the container 10 showing an enlarged neighborhood of the optical paths P1, P2 and P3 according to the first embodiment of the present invention.

FIG. 4 is a plan view of the container 10 showing an enlarged neighborhood of the optical paths P1, P2 and P3 according to the first embodiment of the present invention. It should be noted that the gap between the contour of the DUT 1 and the contour of the plane shape of the gap portion 11 is neglected, and the gap portion 11 is not illustrated.

Referring to FIG. 4, when the terahertz wave which has traveled on the optical path P1 is made incident to the first curved surface portion S1, the enclosure portion 12 serves as a convex lens, and the terahertz wave is refracted toward the optical axis OA. In FIG. 4, the terahertz wave travels downward (optical path P2). The terahertz wave which has traveled on the optical path P2 is made incident to the DUT 1, is refracted, and travels on the optical path P3.

On this occasion, the incident angle and the emission angle of the terahertz wave to and from the DUT 1 are respectively denoted by $\theta_A$ and $\theta_B$. According to Snell's law, there holds a relationship of $(\sin \theta_A)/(\sin \theta_B)=n1/n2$. Moreover, since n1<n2, n1/n2<1 holds. Therefore, there holds $(\sin \theta_A)/(\sin \theta_B)<1$. As a result, $\theta_A<\theta_B$. Accordingly, the optical path P3 departs from the optical axis OA more than a straight extension of the optical path P2. On this occasion, the optical path P3 can be approximately parallel with the optical axis OA by properly setting n2 and the like.

Referring again to FIG. 2, the terahertz wave which has traveled on the optical path P3 inside the DUT 1 is made incident to the enclosure portion 12, is refracted, and travels on the optical path P4 in the enclosure portion 12. The terahertz wave which has traveled on the optical path P4 is made incident to the second curved surface portion S2, is refracted, travels on the optical path P5, and is made incident to the terahertz wave detector 4.

In FIG. 1(a), since the arc representing the first curved surface portion S1 and the arc representing the second curved surface portion S2 are line symmetrical, the light path P2 and the light path P4 are approximately line symmetrical, and the light path P1 and the light path P5 are approximately line symmetrical. Thus, the optical path P5 is located approximately on an extension of the optical path P1.

The terahertz wave detector 4 detects the incident terahertz wave. As a result, the DUT 1 is measured. For example, the DUT 1 includes contents 1a and 1b. Referring to FIG. 2, the terahertz wave transmits through the content 1a, and thus, the position and the like of the content 1a are revealed in a result of the detection of the terahertz wave.

According to the first embodiment, when the terahertz wave is fed to the DUT 1 for the measurement, though the terahertz wave is refracted by the DUT 1, the optical path P5 can be located by the container 10 approximately on the extension of the optical path P1. As a result, the terahertz wave made incident to the terahertz wave detector 4 is in a state similar to a case in which when the container 10 is not present, and the refraction by the DUT 1 almost does not occur. Thus, it is possible to restrain an adverse effect caused by the refraction of the terahertz wave by the DUT 1.

Second Embodiment

Shapes (concaved surfaces) of the first curved surface S1 and the second curved surface S2 of the container 10 according to a second embodiment are different from those (convex surfaces) of the first curved surface S1 and the second curved surface S2 of the container 10 according to the first embodiment.

Figure 5:
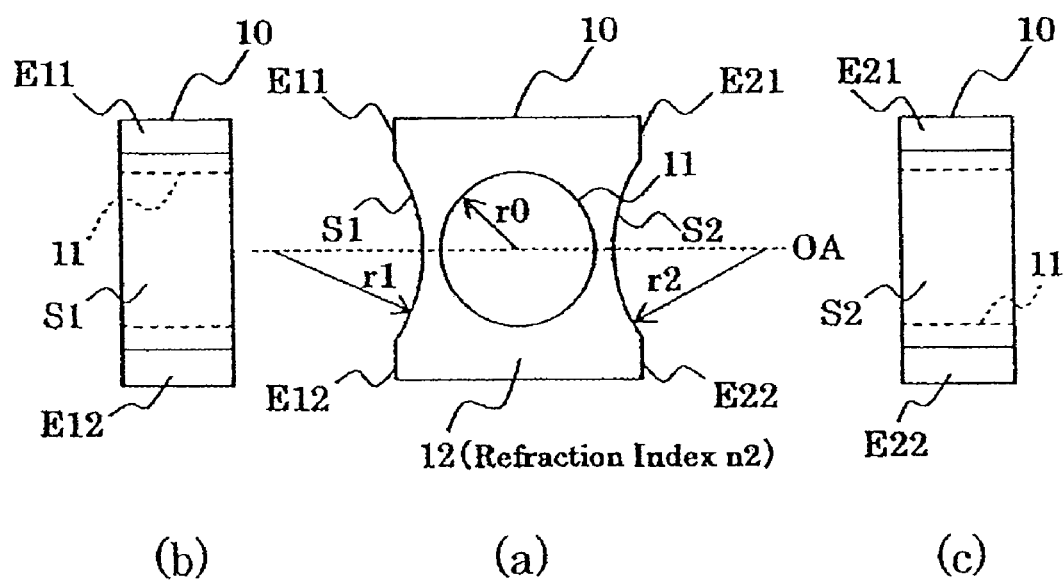
FIG. 5(a) is a plan view of the container 10 according to the second embodiment of the present invention.
FIG. 5(b) is a left side view thereof.
FIG. 5(c) is a right side view thereof.
Figure 6:
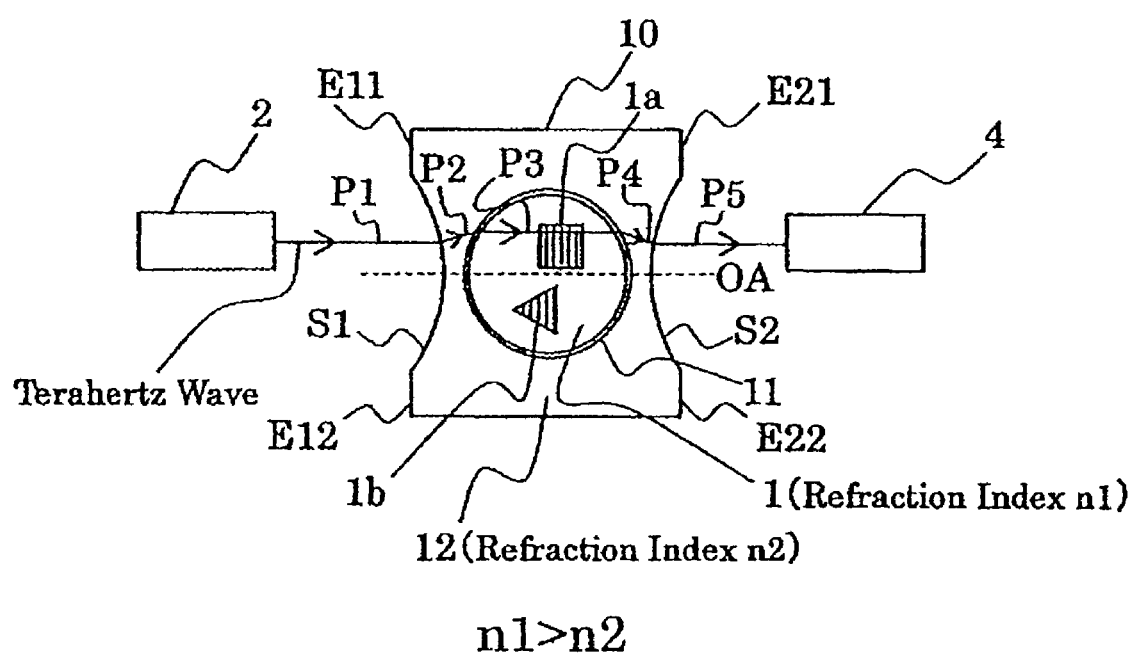
FIG. 6 is a plan view in a state in which at least a part of the DUT 1 is stored in the container 10 according to the second embodiment of the present invention, and the terahertz wave is irradiated on the container 10.

FIG. 5(a) is a plan view of the container 10 according to the second embodiment of the present invention; FIG. 5(b) is a left side view thereof; and FIG. 5(c) is a right side view thereof. FIG. 6 is a plan view in a state in which at least a part of the DUT 1 is stored in the container 10 according to the second embodiment of the present invention, and the terahertz wave is irradiated on the container 10. In the following section, the same components are denoted by the same numerals as of the first embodiment, and will be explained in no more details.

The terahertz wave measurement device is the same as that of the first embodiment, and hence a description thereof is omitted.

The container 10 stores at least a part of the DUT 1 to be measured by the terahertz wave measurement device. It should be noted that the container 10 may store the DUT 1 partially (refer to FIGS. 16(a) and 16(b)) or entirely (refer to FIGS. 17(a) and 17(b)).

The container 10 includes the gap portion 11 and the enclosure portion 12. The gap portion 11 is the same as that of the first embodiment, and hence a description thereof is omitted.

The enclosure portion 12 includes the first curved surface portion S1 and the second curved surface portion S2. The enclosure portion 12 is the same as that of the first embodiment. However, both the first curved surface portion S1 and the second curved surface portion S2 according to the second embodiment are concave surfaces. It should be noted that the refraction index of the DUT 1 is n1, the refraction index of the enclosure portion 12 is n2, and a relationship of n1>n2 holds.

A description will now be given of an operation of the second embodiment.

Referring to FIG. 6, the terahertz wave output device 2 of the terahertz wave measurement device outputs the terahertz wave. The terahertz wave output from the terahertz output device 2 (optical path P1) is irradiated on the first curved surface portion S1. Then, the terahertz wave is refracted, and travels on the optical path P2 in the enclosure portion 12. On this occasion, the thickness of the air layer between the contour of the DUT 1 and the contour of the plane shape of the gap portion 11 is negligible since the thickness is small. The terahertz wave which has traveled on the optical path P2 is made incident to the DUT 1, is refracted, and travels on the optical path P3 inside the DUT 1. It should be noted that the light path P3 is approximately parallel with the light path P1 and the optical axis OA.

Figure 7:
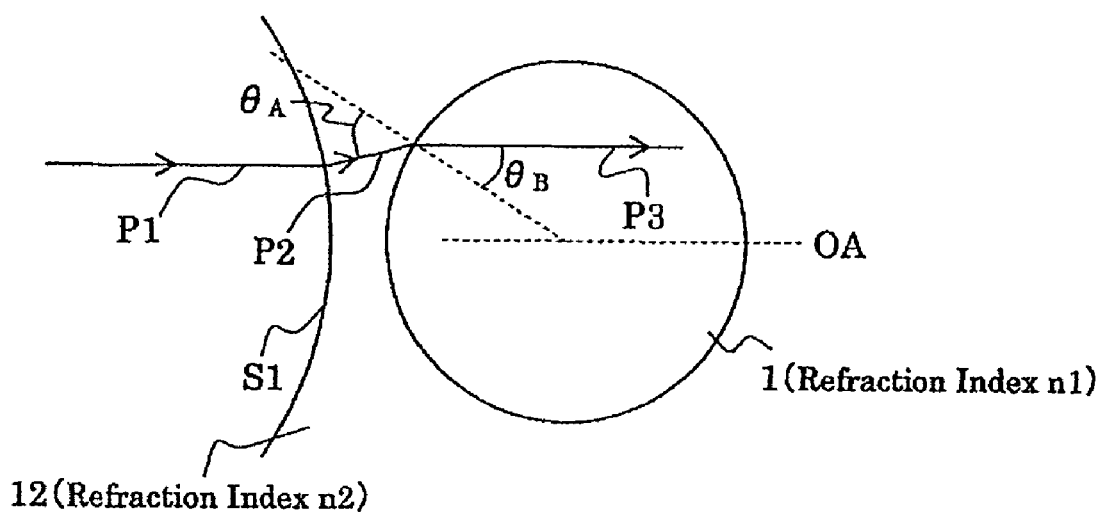
FIG. 7 is a plan view of the container 10 showing an enlarged neighborhood of the optical paths P1, P2 and P3 according to the second embodiment of the present invention.

FIG. 7 is a plan view of the container 10 showing an enlarged neighborhood of the optical paths P1, P2 and P3 according to the second embodiment of the present invention. It should be noted that the gap between the contour of the DUT 1 and the contour of the plane shape of the gap portion 11 is neglected, and the gap portion 11 is not illustrated.

Referring to FIG. 7, when the terahertz wave which has traveled on the optical path P1 is made incident to the first curved surface portion the enclosure portion 12 serves as a concave lens, and the terahertz wave is refracted so as to depart from the optical axis OA. In FIG. 7, the terahertz wave travels upward (optical path P2). The terahertz wave which has traveled on the optical path P2 is made incident to the DUT 1, is refracted, and travels on the optical path P3.

On this occasion, the incident angle and the emission angle of the terahertz wave to and from the DUT 1 are respectively denoted by $\theta_A$ and $\theta_B$. According to Snell's law, there holds a relationship of $(\sin \theta_A)/(\sin \theta_B)=n1/n2$. Moreover, since n1>n2, n1/n2>1 holds. Therefore, there holds $(\sin \theta_A)/(\sin \theta_B)>1$. As a result, $\theta_A>\theta_B$. Accordingly, the optical path P3 approaches the optical axis OA more than a straight extension of the optical path P2. On this occasion, the optical path P3 can be approximately parallel with the optical axis OA by properly setting n2 and the like.

Referring again to FIG. 6, the terahertz wave which has traveled on the optical path P3 inside the DUT 1 is made incident to the enclosure portion 12, is refracted, and travels on the optical path P4 in the enclosure portion 12. The terahertz wave which has traveled on the optical path P4 is made incident to the second curved surface portion S2, is refracted, travels on the optical path P5, and is made incident to the terahertz wave detector 4.

In FIG. 1(a), since the arc representing the first curved surface portion S1 and the arc representing the second curved surface portion S2 are line symmetrical, the light path P2 and the light path P4 are approximately line symmetrical, and the light path P1 and the light path P5 are approximately line symmetrical. Thus, the optical path P5 is located approximately on an extension of the optical path P1.

The terahertz wave detector 4 detects the incident terahertz wave. As a result, the DUT 1 is measured. For example, the DUT 1 includes the contents 1a and 1b. Referring to FIG. 2, the terahertz wave transmits through the content 1a, and thus, the position and the like of the content 1a are revealed in a result of the detection of the terahertz wave.

According to the second embodiment, there are obtained the same effects as in the first embodiment.

Third Embodiment

The container 10 according to a third embodiment is different from the container 10 according to the first embodiment in that the container 10 according to the third embodiment includes an insertion member 20. It should be noted that the provision of the insertion member 20 may be applied to the second embodiment.

Figure 8:
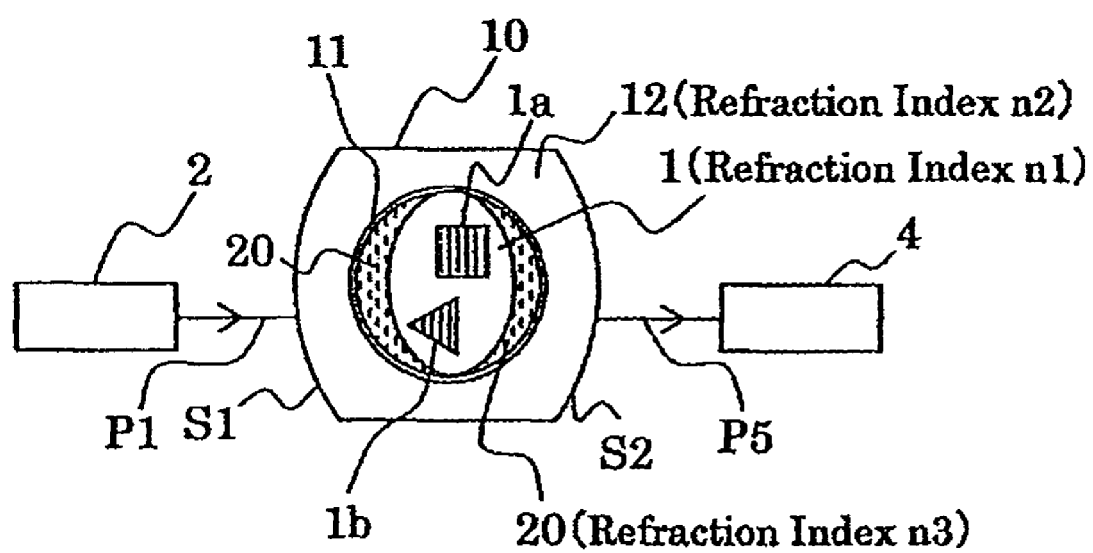
FIG. 8 is a plan view in a state in which at least a part of the DUT 1 is stored in the container 10 according to the third embodiment, and the terahertz wave is irradiated on the container 10.

FIG. 8 is a plan view in a state in which at least a part of the DUT 1 is stored in the container 10 according to the third embodiment, and the terahertz wave is irradiated on the container 10. In the following section, the optical paths P2, P3 and P4 are omitted from the plan views.

The terahertz wave measurement device is the same as that of the first embodiment, and hence a description thereof is omitted. It should be noted that the end planes E11, E12, E21 and E22 are not illustrated in FIGS. 8 to 20.

The plane shape of the DUT 1 is obtained by removing a part of the circle with the radius r-g (refer to FIG. 3). In FIG. 8, the plane shape of the DUT 1 is an ellipse with a major axis of r-g. Thus, the DUT 1 is an elliptic cylinder with a bottom surface of the ellipse with the major axis of r-g.

The insertion member 20 is inserted in a space between the DUT 1 and the gap portion 11. A contour of a plane shape (shape and plane cross section viewed from above) of an integrated body of the DUT 1 and the insertion member 20 is the circle with the radius of r-g. Thus, the DUT 1 and the insertion member 20 constitute the cylinder with a bottom of the circle with the radius of r-g. The contour (circle with the radius of r-g) of the plane shape of the integrated body of the DUT 1 and the insertion member 20 forms concentric circles along with the contour (circle with the radius of r) of the plane shape of the gap portion 11. It should be noted that $g \leq \lambda/4$ preferably holds as in the first embodiment.

It should be noted that g denotes a distance between the contour (circle with the radius of r-g) of the plane shape of the integrated body of the DUT 1 and the insertion member 20 and the contour (circle with the radius of r) of the plane shape of the gap portion 11. It should be noted that $\lambda$ is the wavelength of the terahertz wave output from the terahertz wave output device 2 of the terahertz wave measurement device toward the DUT 1.

On this occasion, the refraction index of the DUT 1 is n1, and the refraction index of the insertion member 20 is n3. Then, there holds $n1-0.1 \leq n3 \leq n1+0.1$. It is preferable that n1=n3 holds. Moreover, n1 and n3 may not be equal to the refraction index (such as 1) of the atmosphere of the container 10.

An operation of the third embodiment is approximately the same as that of the first embodiment. However, the third embodiment is different from the first embodiment in a point that the terahertz wave transmits also through the insertion member 20. If the thickness g of the air layer is neglected, and there holds n1=n3, the optical paths of the terahertz wave is the same as those of the first embodiment.

According to the third embodiment, there are obtained the same effects as in the first embodiment.

Moreover, even if the DUT 1 is not a cylinder, since the insertion member 20 serves to integrate the DUT 1 and the insertion member 20 into a cylinder, the DUT 1 can be treated as a cylinder according to the third embodiment.

The description has been given of the third embodiment assuming that the DUT 1 is an elliptic cylinder. However, the DUT 1 may not be a solid of revolution such as an elliptic cylinder. It is only necessary for the integrated body of the DUT 1 and the insertion member 20 to form a cylinder.

Moreover, the container 10 may include, in place of the insertion member 20, a filling material (a liquid such as oil, for example) filled in the space between the DUT 1 and the gap portion 11. When the refraction index of the filling material is n4 and the refraction index of the DUT 1 is n1, there holds $n1-0.1 \leq n4 \leq n1+0.1$. It is preferable that n1=n4 holds. Moreover, n1 and n4 may not be equal to the refraction index (such as 1) of the atmosphere of the container 10.

Fourth Embodiment

A fourth embodiment is different from the first embodiment in arrangement of the container 10 with respect to the terahertz wave measurement device. It should be noted that the arrangement according to the fourth embodiment may be applied to the second embodiment.

Figure 9:
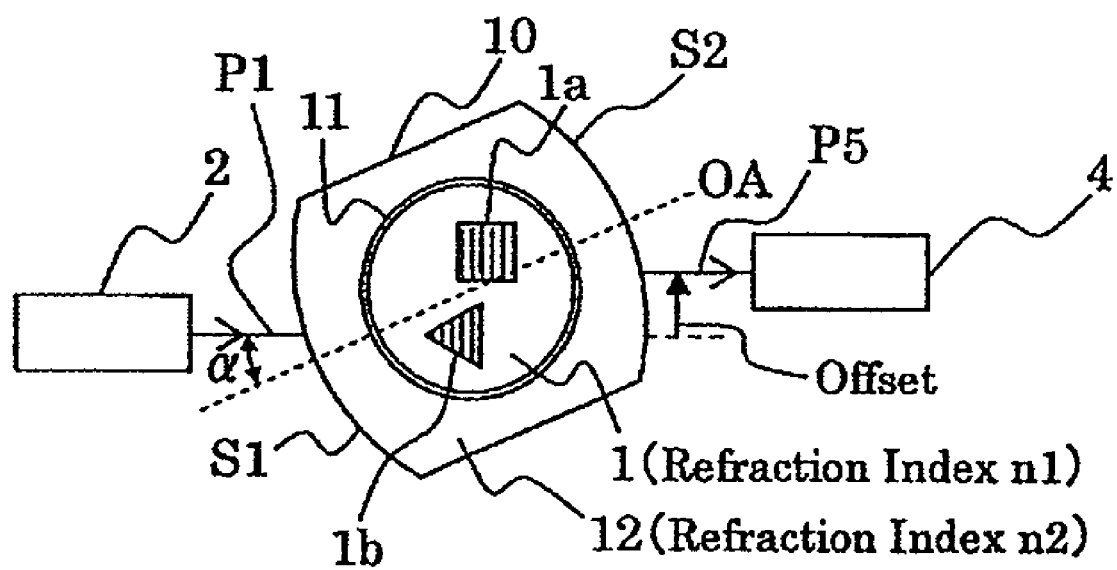
FIG. 9 is a plan view in a state in which at least a part of the DUT 1 is stored in the container 10 according to the fourth embodiment, and the terahertz wave is irradiated on the container 10.

FIG. 9 is a plan view in a state in which at least a part of the DUT 1 is stored in the container 10 according to the fourth embodiment, and the terahertz wave is irradiated on the container 10.

Configurations of the container 10 and the terahertz wave measurement device are the same as those in the first embodiment, and a description thereof, therefore, is omitted.

It should be noted that, referring to FIG. 9, the optical axis OA of the first curved surface portion S1 intersects with the traveling direction (optical path P1) of the terahertz wave output from the terahertz wave output device 2 of the terahertz wave measurement device toward the DUT 1 at an angle α, which is more than 0 degree and less than 90 degrees. The container 10 is provided so as to measure the DUT 1 by the terahertz wave measurement device.

A description will now be given of an operation of the fourth embodiment.

Referring to FIG. 9, since the optical axis OA of the first curved surface portion S1 intersects with the optical path P1 at the angle of a (more than 0 degree and less than 90 degrees), the optical path of the terahertz wave output from the terahertz wave output device 2 is displaced by a predetermined distance (offset), and the terahertz wave travels on the optical path P5, and is made incident to the terahertz wave detector 4.

The terahertz wave detector 4 detects the incident terahertz wave. As a result, the DUT 1 is measured.

According to the fourth embodiment, there are obtained the same effects as in the first embodiment.

Moreover, according to the fourth embodiment, the optical path of the terahertz wave output from the terahertz wave output device 2 is displaced by a predetermined distance (offset), and the terahertz wave is made incident to the terahertz wave detector 4. As a result, the fourth embodiment is suitable for a case in which the terahertz wave detector 4 is not present in the traveling direction of the terahertz wave output from the terahertz wave output device 2.

Fifth Embodiment

A fifth embodiment is different from the first embodiment in that enclosure portions 12a and 12b can be separated along separation surfaces D1 and D2. It should be noted that, in the container 10 according to the second embodiment, the enclosure portions 12a and 12b may be separated along the separation surfaces D1 and D2 as indicated in the fifth embodiment.

Figure 10:
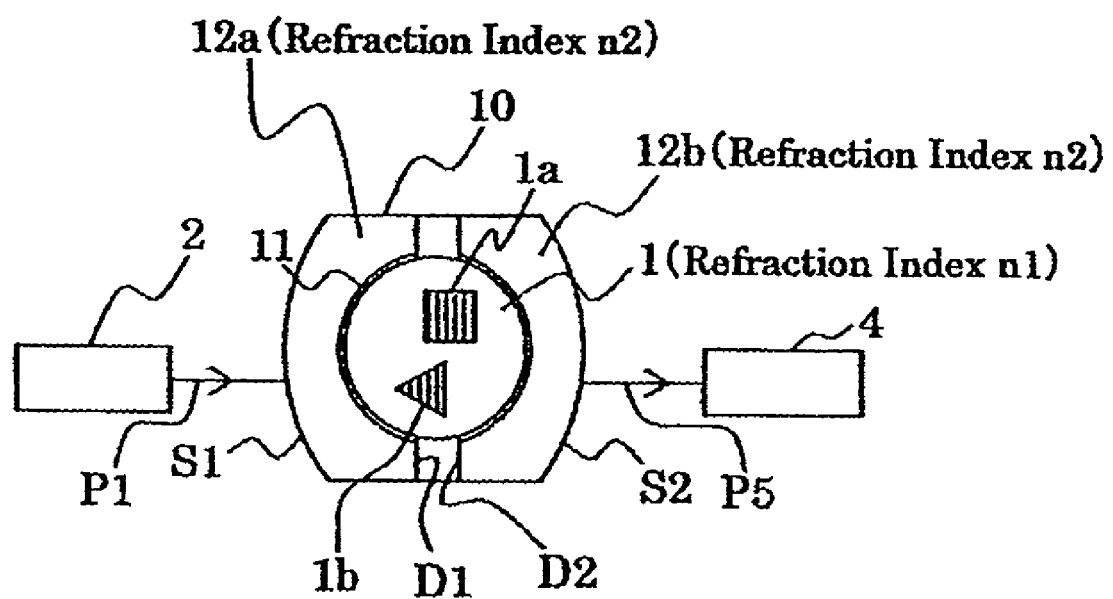
FIG. 10 is plan view in a state in which at least a part of the DUT 1 is stored in the container 10 according to the fifth embodiment, and the terahertz wave is irradiated on the container 10.
Figure 11:
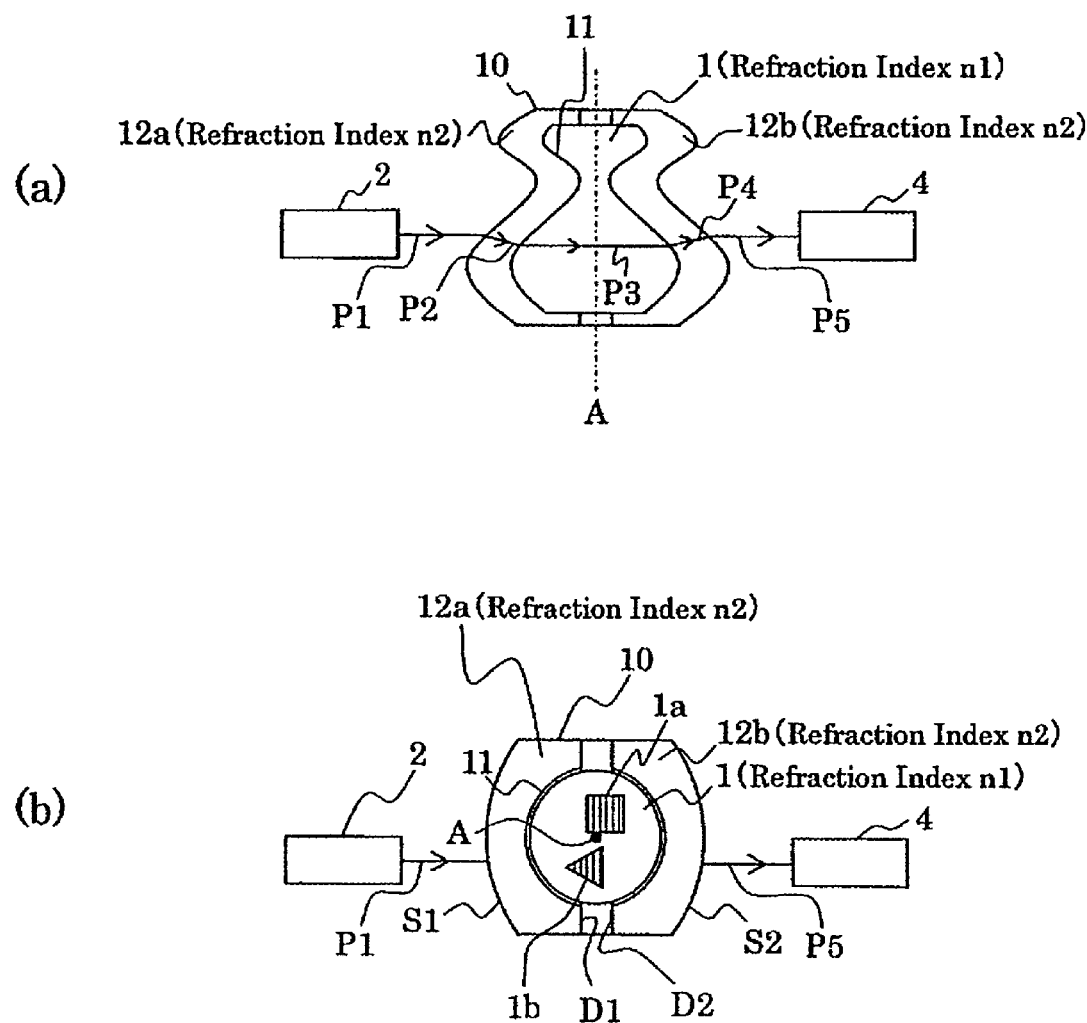
FIG. 11(a) is a front cross sectional view.
FIG. 11(b) is a plan cross sectional view when the DUT 1 is stored in the container 10 according to the sixth embodiment.

FIG. 10 is plan view in a state in which at least a part of the DUT 1 is stored in the container 10 according to the fifth embodiment, and the terahertz wave is irradiated on the container 10.

The configurations of the container 10 and the terahertz wave measurement device are approximately the same as those of the first embodiment. It should be noted that the container 10 includes the enclosure portions 12a and 12b in place of the enclosure portion 12. The enclosure portions 12a and 12b can be separated along the separation surfaces D1 and D2. Moreover, the separation surfaces D1 and D2 intersect with the gap portion 11. It should be noted that the separation surfaces D1 and D2 may be separated from each other as shown in FIG. 10. Moreover, the enclosure portions 12a and 12b are coupled to each other by coupling means, which is not shown. In the case shown in FIG. 10, the contour of a plane shape of the gap portion 11 includes an arc protruding leftward and an arc protruding rightward.

An operation of the fifth embodiment is the same as the operation of the first embodiment, and hence a description thereof is omitted.

With the container 10 according to the fifth embodiment, since the enclosure portions 12a and 12b can be separated along the separation surfaces D1 and D2, the DUT 1 can be easily stored in the gap portion 11. For example, the enclosure portions 12a and 12b are separated along the separation surfaces D1 and D2, and the DUT 1 is then stored inside the gap portion 11. Then, the enclosure portions 12a and 12b may be coupled to each other by the coupling means, which is not shown.

Sixth Embodiment

The container 10 according to a sixth embodiment is obtained by modifying the container 10 according to the first embodiment so as to deal with a case in which the diameter of the DUT 1 changes according to the height thereof.

FIG. 11(a) is a front cross sectional view, and FIG. 11(b) is a plan cross sectional view when the DUT 1 is stored in the container 10 according to the sixth embodiment. It should be noted that the gap between the container 10 and the gap portion 11 is omitted for the sake of illustration in FIG. 11(a). Moreover, FIG. 11(b) is a cross sectional view made on a plane including the optical path P1, and crossing the container 10 and the DUT 1.

Referring to FIGS. 11(a) and 11(b), the DUT 1 is a solid of revolution, and the center axis of the solid of revolution is a line A (refer to FIGS. 16(a), 16(b), 17(a) and 17(b)) extending vertically (Z direction). The diameter of the plane cross section of the DUT 1 changes according to the height of the plane cross section. Therefore, as shown in FIG. 11(a), for example, the contour in the front sectional view of the DUT 1 is formed as a result of a combination of a convex surface, a concave surface, and a convex surface arranged from the top.

Referring to FIG. 11(a), according to the contour in the front section of the DUT 1, the radii of the contours of the plane cross sections of the gap portion 11, and the enclosure portions 12a and 12b change along the height of the gap portion 11 and the enclosure portions 12a and 12b. Thus, the contours of the front sections of the gap portion 11 and the enclosure portions 12a and 12b are also formed as a result of a combination of a convex surface, a concave surface, and a convex surface arranged from the top.

Referring to FIG. 11(b), the enclosure portions 12a and 12b can be separated along the separation surfaces D1 and D2. Moreover, the separation surfaces D1 and D2 intersect with the gap portion 11 (which is the same as the fifth embodiment). As a result, the DUT 1 can be easily stored in the gap portion 11. For example, the enclosure portions 12a and 12b are separated along the separation surfaces D1 and D2, and the DUT 1 is then stored inside the gap portion 11. Then, the enclosure portions 12a and 12b may be coupled to each other by the coupling means, which is not shown.

It should be noted that the positions of the terahertz wave output device 2 and the terahertz wave detector 4 of the terahertz wave measurement device and the positions of the optical paths P1 and P2 in FIG. 11(b) are the same as those in FIG. 10, and hence a description thereof is omitted.

However, a description will be given of the optical paths P1 to P5 in FIG. 11(a). The optical path P1 enters a part of the front cross section of the gap portion 11 corresponding to the convex surface. Moreover, the front cross section of the gap portion 11 is line-symmetrical about the line A as the axis of symmetry. Thus, as in the first embodiment in which the terahertz wave enters the first curved surface portion S1, which is the convex surface (refer to FIGS. 2 and 3), the terahertz wave is refracted, and the optical path P5 is to be situated on the extension of the optical path P1.

With the container 10 according to the sixth embodiment, since the contours of the front cross sections of the gap portion 11 and the enclosure portions 12a and 12b are formed by the curved surfaces according to the change in the shape of the DUT 1 in the vertical direction, the optical path P5 can be situated on the extension of the optical path P1.

Seventh Embodiment

The container 10 according to a seventh embodiment of the present invention approximately corresponds to a case in which the enclosure portions 12a and 12b of the container 10 according to the fifth embodiment are made different from each other in shape.

FIGS. 12(a) and 12(b) are plan views of the container 10 according to the seventh embodiment of the present invention. It should be noted that FIG. 12(a) is a plan view of the container 10 when n2a>n1 and n2b>n1. FIG. 12(b) is a plan view of the container 10 when n2a<n1 and n2b>n1.

The terahertz wave measurement device is the same as that of the first embodiment, and hence a description thereof is omitted. It should be noted that the electromagnetic wave to be output and detected by the terahertz wave measurement device (electromagnetic wave measurement device) is not limited to the terahertz wave, and may be an electromagnetic wave the frequency of which is equal to or more than 0.01 [THz] and equal to or less than 100 [THz] as in the first embodiment.

The container 10 stores at least a part of the DUT 1 to be measured by the terahertz wave measurement device. It should be noted that the container 10 may store the DUT 1 partially (refer to FIGS. 16(a) and 16(b)) or entirely (refer to FIGS. 17(a) and 17(b)).

The container 10 includes a first cover portion 13a and a second cover portion 13b. A material of the first cover portion 13a and the second cover portion 13b may be the same as the material of the enclosure portion 12.

The refraction index of the first cover portion 13a is n2a. The first cover portion 13a includes the first curved surface portion S1 (same as the first and second embodiments), and a first concave portion 11a. The first curved surface portion S1 receives the terahertz wave output from the terahertz wave output device 2 of the terahertz wave measurement device toward the DUT 1. The first concave portion 11a is closer to the DUT 1 than the first curved surface portion S1, and transmits the terahertz wave.

On this occasion, when n2a is larger than n1 (refraction index of the DUT 1), referring to FIG. 12(a), the first curved surface portion S1 is a convex surface. The specific shape of the first curved surface portion S1 is the same as that of the first embodiment.

When n2a is less than n1, referring to FIG. 12(b), the first curved surface portion S1 is a concave surface. The specific shape of the first curved surface portion S1 is the same as that of the second embodiment.

The refraction index of the second cover portion 13b is n2b. The second cover portion 13b includes the second curved surface portion S2 (same as the first and second embodiments), and a second concave portion 11b. The second concave portion 11b receives the terahertz wave which has transmitted through the DUT 1. The second curved portion S2 is farther than the second concave portion 11b from the DUT 1, and transmits the terahertz wave.

On this occasion, when n2b is larger than n1, referring to FIG. 12(a), the second curved surface portion S2 is a convex surface. The specific shape of the second curved surface portion S2 is the same as that of the first embodiment.

When n2b is less than n1, referring to FIG. 12(b), the second curved surface portion S2 is a concave surface. The specific shape of the second curved surface portion S2 is the same as that of the second embodiment.

It should be noted that n2a and n2b are different from each other. Moreover, the curvature radius of the plane shape of the first curved surface portion S1 and the curvature radius of the plane shape of the second curved surface portion S2 are different from each other. In FIGS. 12(a) and 12(b), the curvature radius of the plane shape of the second curved surface portion S2 is larger than the curvature radius of the plane shape of the first curved portion S1.

Moreover, the contours of the plane shapes of the first concave portion 11a and the second concave portion 11b are arcs. A distance between the contours of the plane shapes of the first concave portion 11a and the second concave portion 11b, and the contour of the plane shape of the DUT 1 is g1. It should be noted that $g1 \leq \lambda/4$ preferably holds as in the first embodiment (refer to FIG. 3).

It should be noted that the optical as OA (which is the same as that in FIG. 2, and is thus omitted) of the first curved surface portion S1 is also set parallel with the traveling direction (optical path P1) of the terahertz wave output from the terahertz wave output device 2 of the terahertz wave measurement device toward the DUT 1 as in the first embodiment (refer to FIG. 2).

It should be noted that the optical axis OA of the first curved surface portion S1 may intersect with the optical path P1 at the angle α, which is more than 0 degree and less than 90 degrees (as in the fourth embodiment and as shown in FIG. 9).

It should be noted that the DUT 1 is stored in the container 10, and, then, the first cover portion 13*a* and the second cover portion 13*b* are coupled by coupling means which is not shown.

A description will now be given of an operation of the seventh embodiment.

Figure 12:
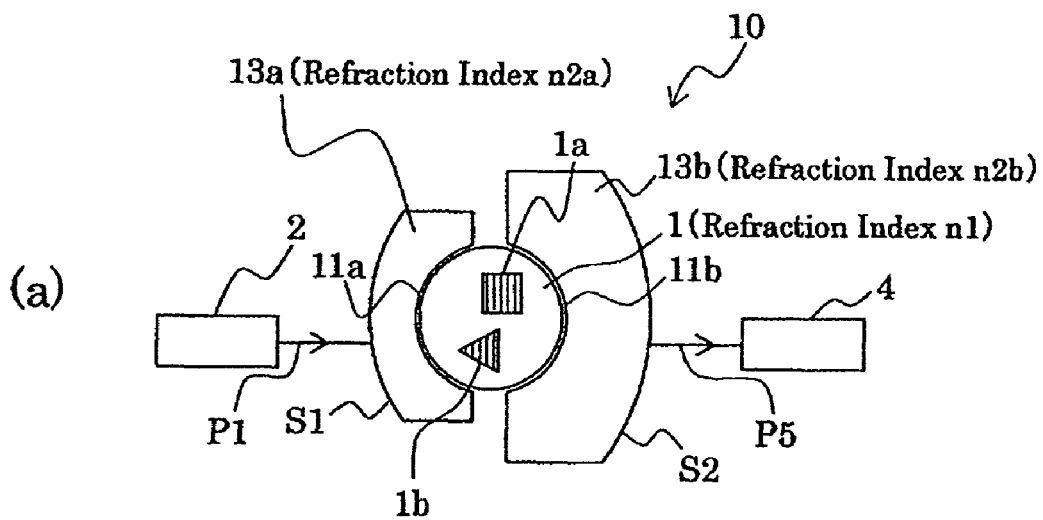
FIGS. 12(a) and 12(b) are plan views of the container 10 according to the seventh embodiment of the present invention.
Figure 12:
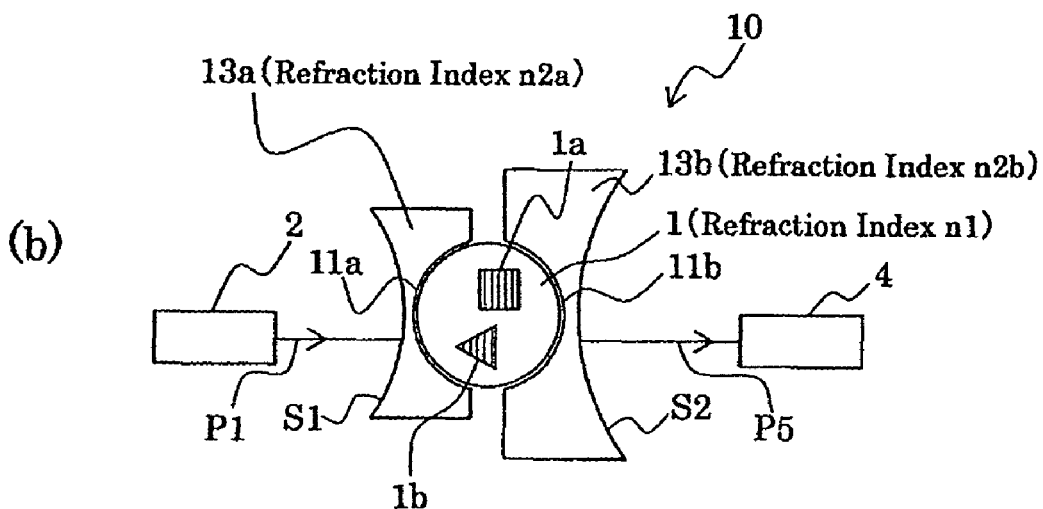
Figure 13:
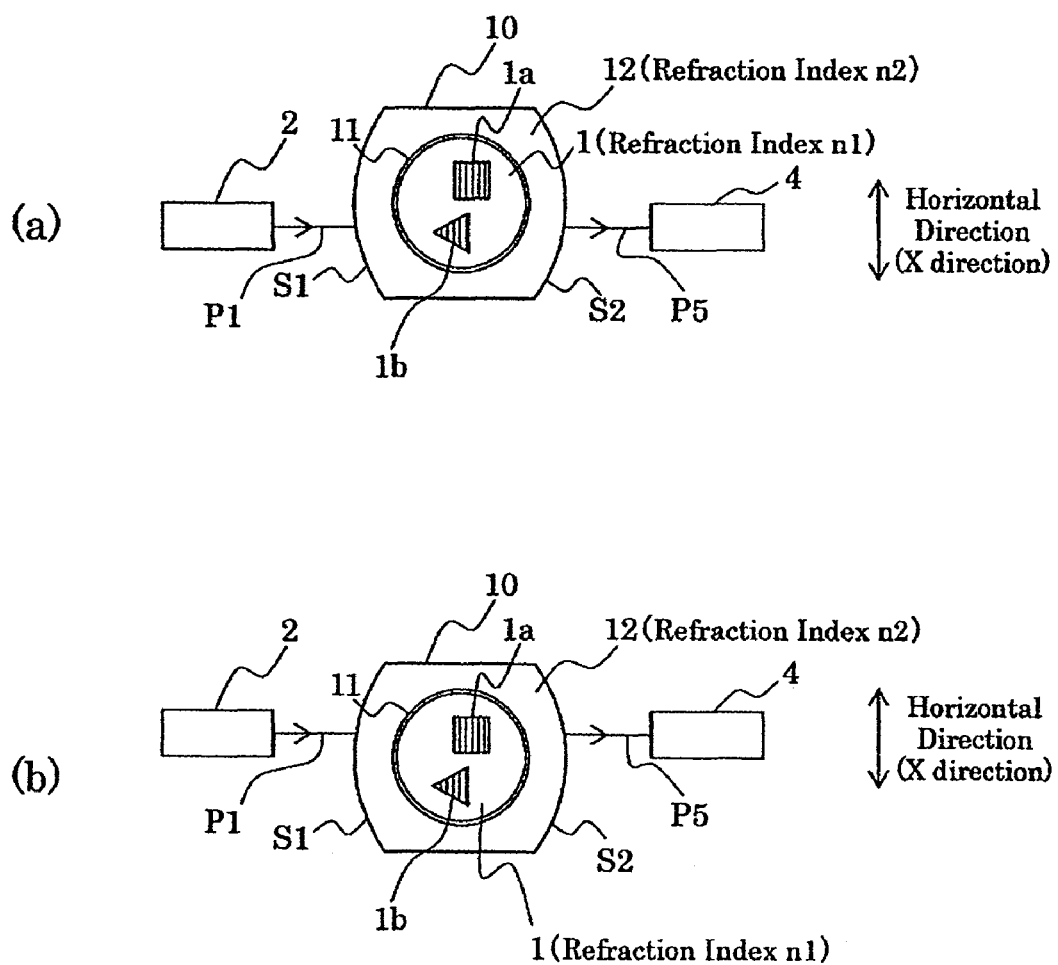
FIGS. 13(a) and 13(b) are plan views of the container 10 and the terahertz wave measurement device for describing the operation of the tenth embodiment.
Figure 14:
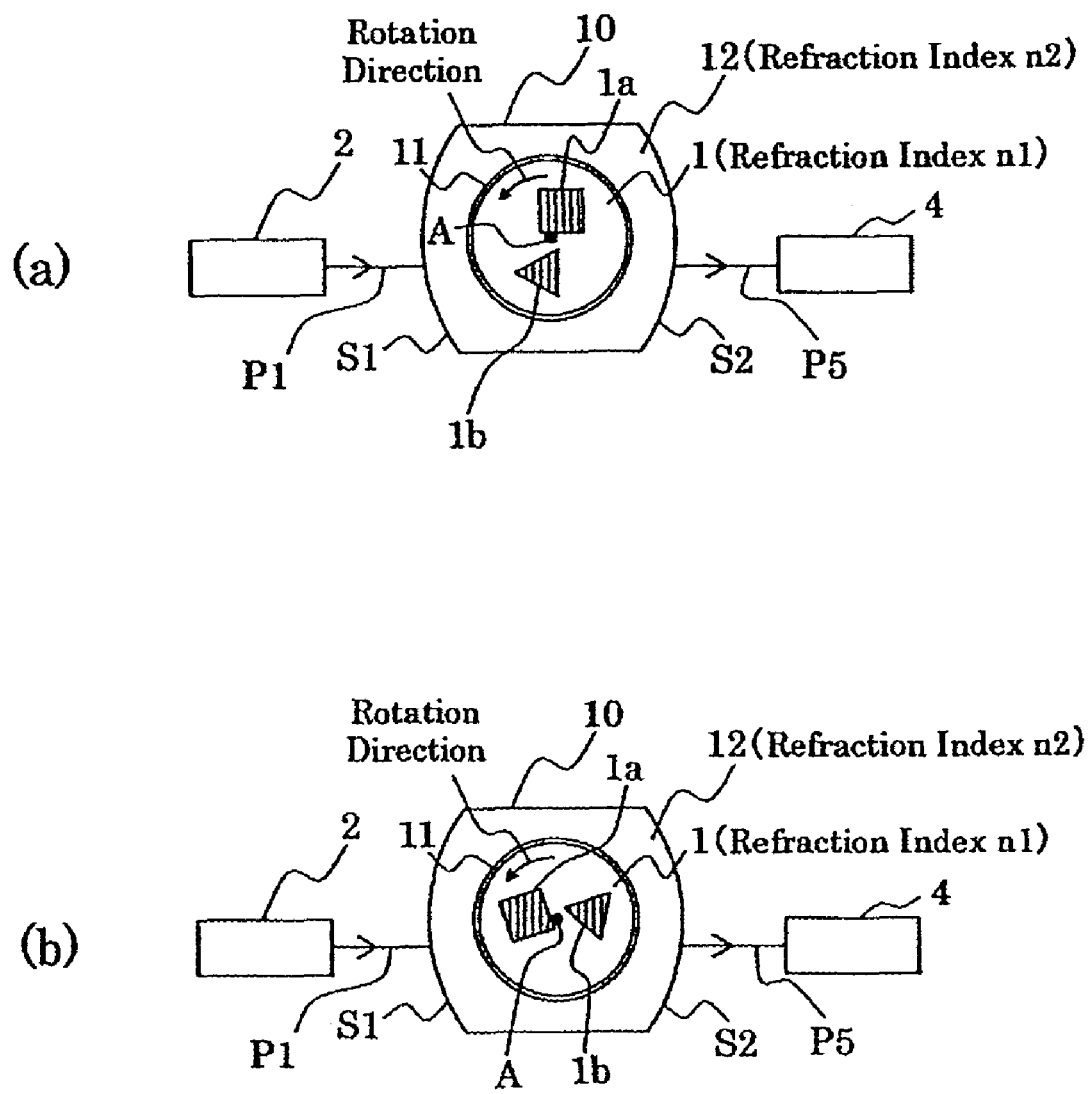
FIGS. 14(a) and 14(b) are plan views of the container 10 and the terahertz wave measurement device for describing the operation of the eleventh embodiment.
Figure 15:
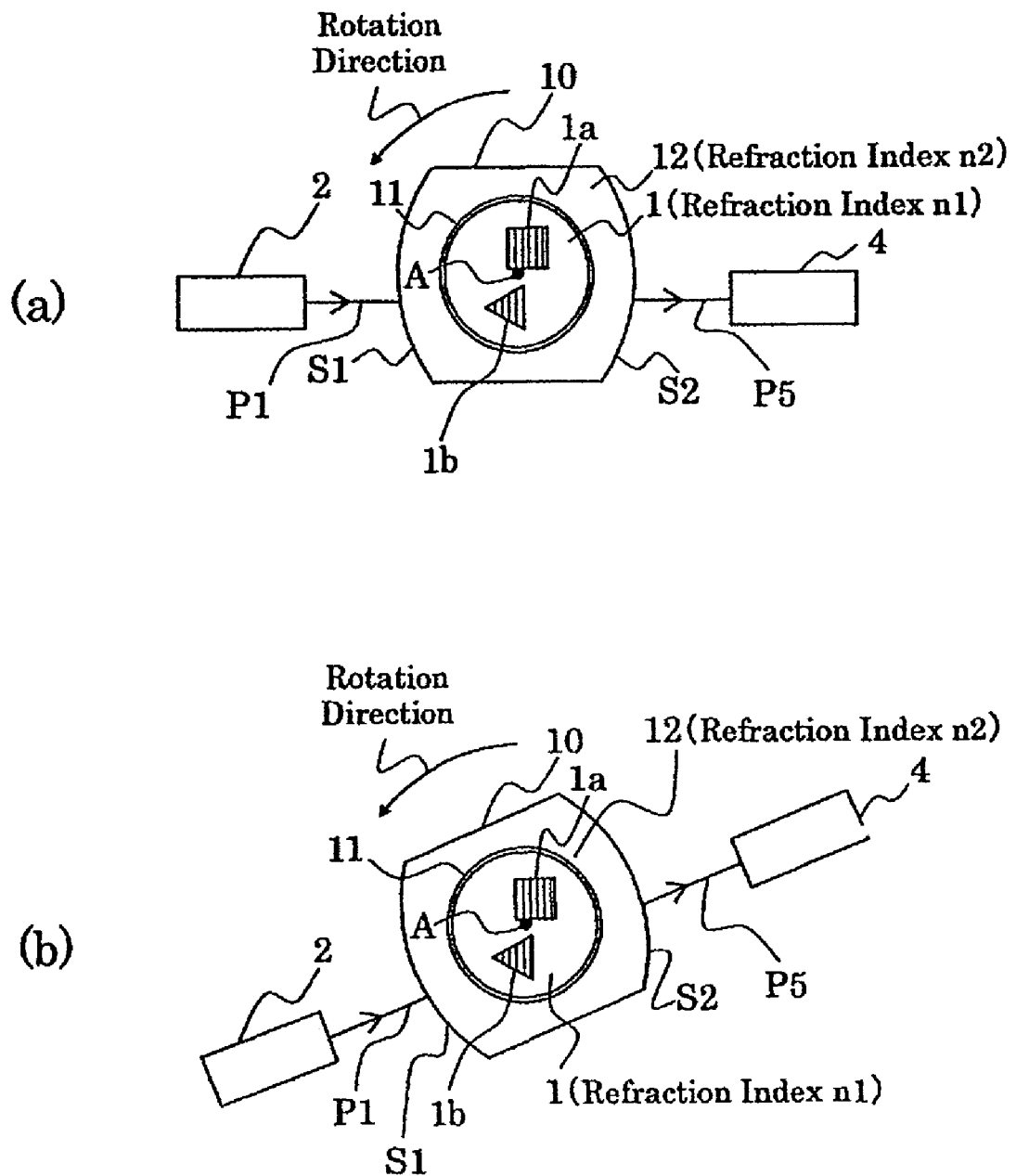
FIGS. 15(a) and 15(b) are plan views of the container 10 and the terahertz wave measurement device for describing the operation of the twelfth embodiment.

With the container 10 shown in FIG. 12(*a*), the terahertz wave travels on the same optical paths as those of the first embodiment. It should be noted that, by properly setting the curvature radii of the plane shapes of the first curved surface portion S1 and the second curved surface portion S2, n2*a*, and n2*b*, the optical path P5 is to be situated approximately on the extension of the optical path P1.

With the container 10 shown in FIG. 12(*b*), the terahertz wave travels on the same optical paths as those of the second embodiment. It should be noted that, by properly setting the curvature radii of the plane shapes of the first curved surface portion S1 and the second curved surface portion S2, n2*a*, and n2*b*, the optical path P5 is situated approximately on the extension of the optical path P1.

According to the seventh embodiment, there are obtained the same effects as in the first embodiment.

As the seventh embodiments, the description has been given of the case in which n1<n2*a* and n1<n2*b* (refer to FIG. 12(*a*)), and the case in which n1>n2*a* and n1>n2*b* (refer to FIG. 12(*b*)). However, a case in which n1<n2*a* and n1>n2*b*, and a case in which n1>n2*a* and n1<n2*b* are conceivable.

Figure 18:
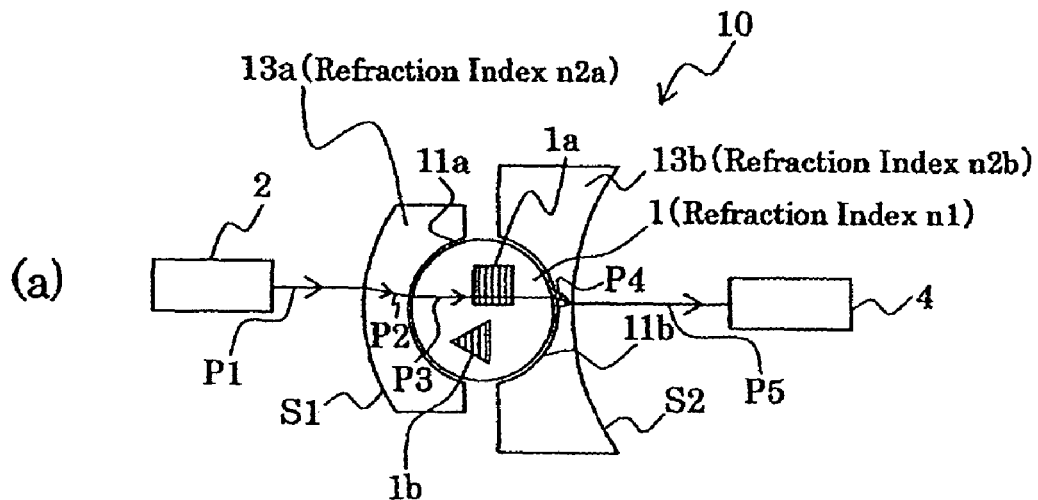
FIGS. 18(a) and 18(b) show variations of the seventh embodiment.
Figure 18:
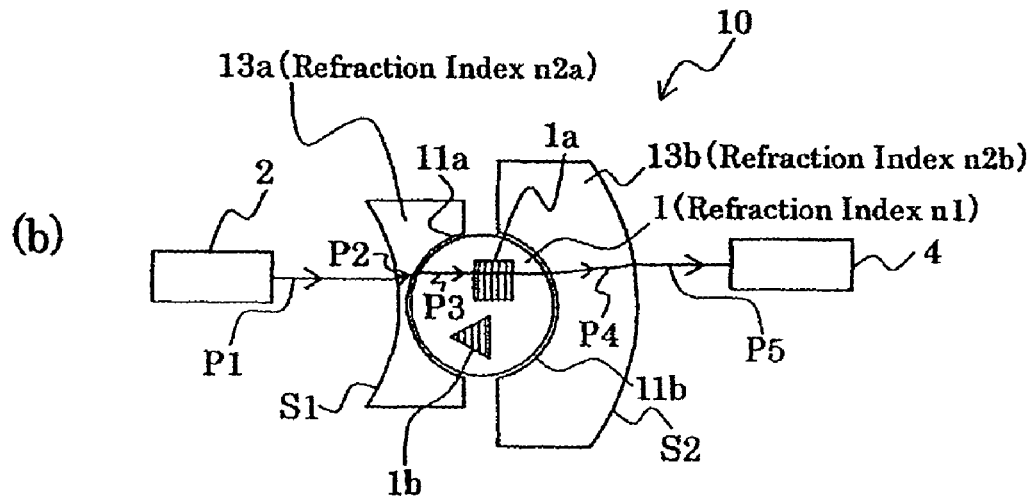

FIGS. 18(*a*) and 18(*b*) show variations of the seventh embodiment. It should be noted that FIG. 18(*a*) is a plan view of the container 10 when n1<n2*a* and n1>n2*b*. FIG. 18(*b*) is a plan view of the container 10 when n1>n2*a* and n1<n2*b*.

In FIG. 18(*a*), the first curved surface portion S1 is a convex surface and the second curved surface portion S2 is a concave surface. The optical paths P1, P2 and P3 are the same as those of the first embodiment (refer to FIG. 2), and the optical paths P4 and P5 are the same as those of the second embodiment (refer to FIG. 6). Though the optical path P5 is not situated on the extension of the optical path P1, the optical path P5 and the optical path P1 can be approximately parallel with each other.

In FIG. 18(*b*), the first curved surface portion S1 is a concave surface and the second curved surface portion S2 is a convex surface. The optical paths P1, P2 and P3 are the same as those of the second embodiment (refer to FIG. 6), and the optical paths P4 and P5 are the same as those of the first embodiment (refer to FIG. 2). Though the optical path P5 is not situated on the extension of the optical path P1, the optical path P5 and the optical path P1 can be approximately parallel with each other.

Eighth Embodiment

The container 10 according to an eighth embodiment is different from the container 10 according to the seventh embodiment in that the container 10 according to the eighth embodiment includes the insertion member 20.

Figure 19:
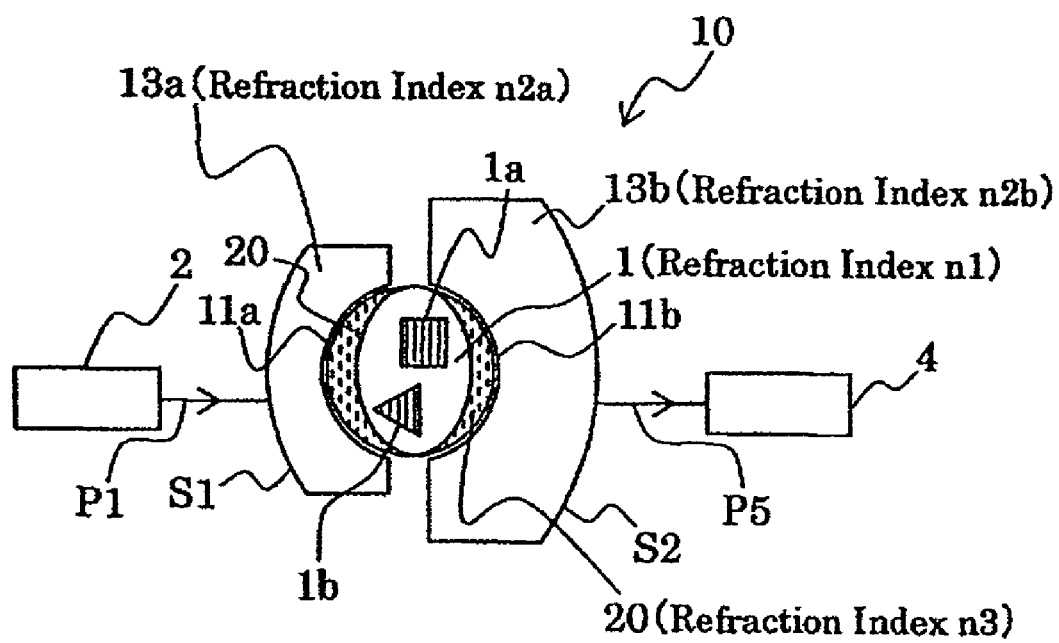
FIG. 19 is a plan view in a state in which at least a part of the DUT 1 is stored in the container 10 according to the eighth embodiment, and the terahertz wave is irradiated on the container 10.

FIG. 19 is a plan view in a state in which at least a part of the DUT 1 is stored in the container 10 according to the eighth embodiment, and the terahertz wave is irradiated on the container 10. Though a case in which n1<n2*a* and n1<n2*b* is shown, the eighth embodiment may be applied to other cases (refer to FIG. 12(*b*), FIG. 18(*a*) and FIG. 18(*b*)).

The terahertz wave measurement device is the same as that of the first embodiment, and hence a description thereof is omitted. The plane shape of the DUT 1 is the same as that of the third embodiment.

The insertion member 20 is inserted in a space between the DUT 1 and the first concave portion 11*a* and the second concave portion 11*b*. The plane shape of an integrated body of the DUT 1 and the insertion member 20 is a circle with the radius of r-g as in the third embodiment. The contour (circle with the radius of r-g) of the plane shape of the integrated body of the DUT 1 and the insertion member 20 forms concentric circles along with the contours (parts of the circle with the radius of r) of the plane shapes of the first concave portion 11*a* and the second concave portion 11*b*. It should be noted that $g \leq \lambda/4$ preferably holds as in the first embodiment.

It should be noted that g denotes a distance between the contour (circle with the radius of r-g) of the plane shape of the integrated body of the DUT 1 and the insertion member 20 and the contours (circle with the radius of r) of the plane shapes of the first concave portion 11*a* and the second concave portion 11*b*. It should be noted that $\lambda$ is the wavelength of the terahertz wave output from the terahertz wave output device 2 of the terahertz wave measurement device toward the DUT 1.

On this occasion, the refraction index of the DUT 1 is n1, and the refraction index of the insertion member 20 is n3. Then, there holds $n1-0.1 \leq n3 \leq n1+0.1$. It is preferable that n1=n3 holds. Moreover, n1 and n3 may not be equal to the refraction index (such as 1) of the atmosphere of the container 10.

An operation of the eighth embodiment is approximately the same as that of the seventh embodiment. However, the eighth embodiment is different from the seventh embodiment in a point that the terahertz wave transmits also through the insertion member 20. If the thickness g of the air layer is neglected, and there holds n1=n3, the optical path of the terahertz wave is the same as that of the seventh embodiment.

According to the eighth embodiment, there are obtained the same effects as in the seventh embodiment.

Moreover, even if the DUT 1 is not a cylinder, since the insertion member 20 serves to integrate the DUT 1 and the insertion member 20 into a cylinder, the DUT 1 can be treated as a cylinder according to the eighth embodiment.

The description has been given of the eighth embodiment assuming that the DUT 1 is an elliptic cylinder. However, the DUT 1 may not be a solid of revolution such as an elliptic cylinder. It is only necessary for the integrated body of the DUT 1 and the insertion member 20 to form a cylinder.

Moreover, the container 10 may be provided with, in place of the insertion member 20, a filling material (a liquid such as oil, for example) filled in the space between the DUT 1 and the first concave portion 11*a* and the second concave portion 11*b*. When the refraction index of the filling material is n4 and the refraction index of the DUT 1 is n1, there holds $n1-0.1 \leq n4 \leq n1+0.1$. It is preferable that n1=n4 holds. Moreover, n1 and n4 may not be equal to the refraction index (such as 1) of the atmosphere of the container 10.

Ninth Embodiment

The container 10 according to a ninth embodiment is obtained by modifying the container 10 according to the seventh embodiment so as to deal with a case in which the diameter of the DUT 1 changes according to the height thereof.

Figure 20:
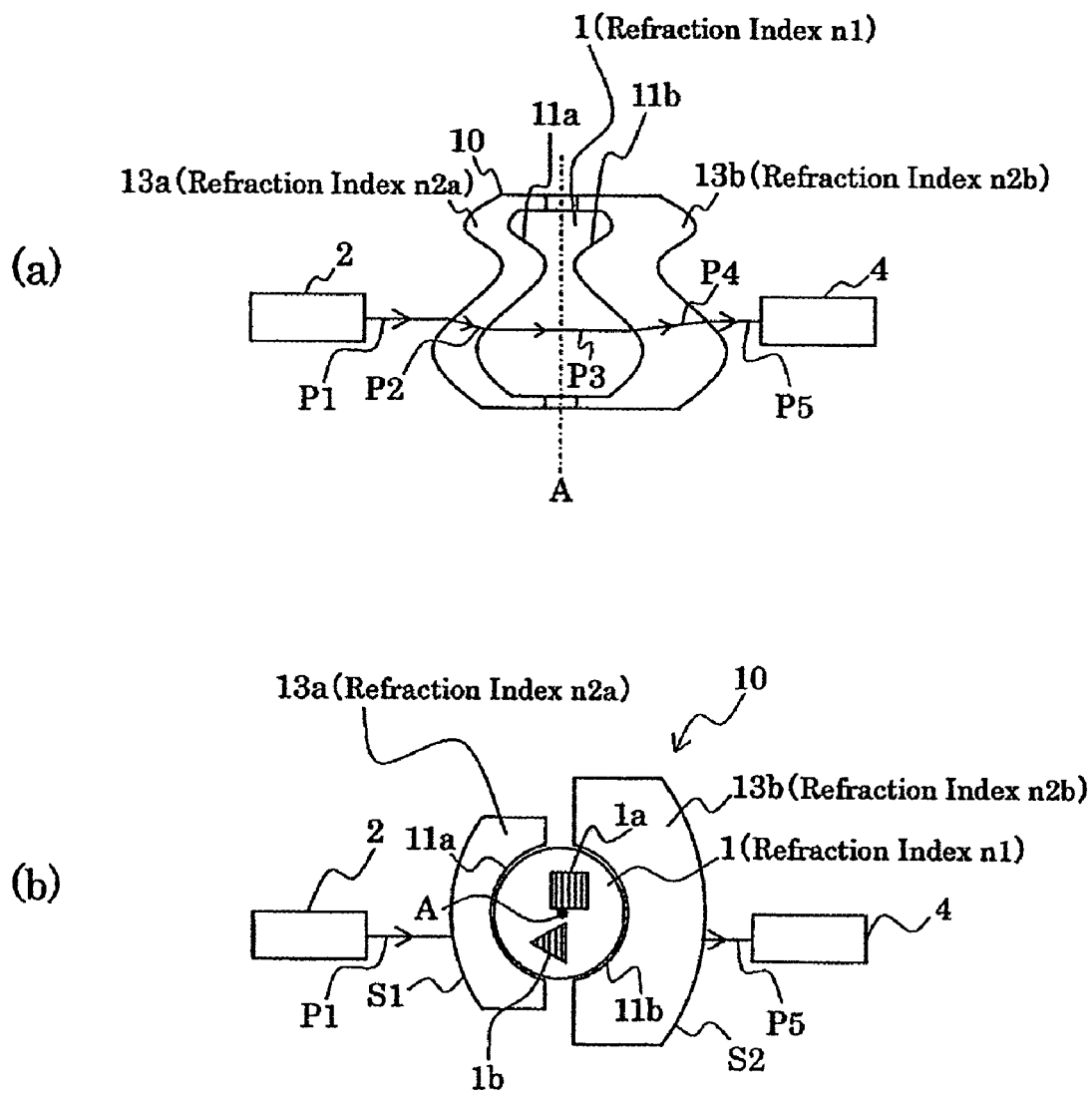
FIG. 20(a) is a front cross sectional view.
FIG. 20(b) is a plan cross sectional view when the DUT 1 is stored in the container 10 according to the ninth embodiment.
Figure 21:
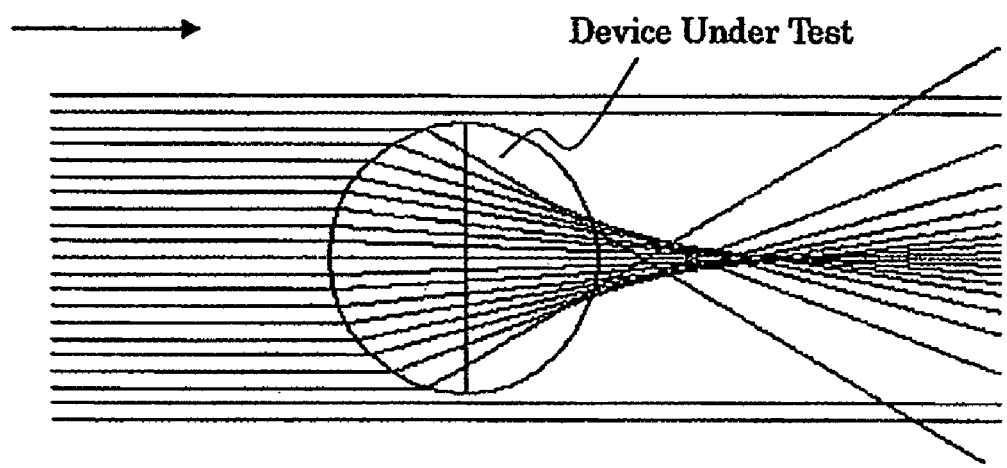
FIG. 21 shows estimated optical paths of the terahertz wave when the refraction index of a conventional device under test is 1.4, and the refraction index of the ambient air of the device under test is 1.

FIG. 20(*a*) is a front cross sectional view, and FIG. 20(*b*) is a plan cross sectional view when the DUT 1 is stored in the container 10 according to the ninth embodiment. It should be noted that the gap between the container 10 and the gap portion 11 is omitted for the sake of illustration in FIG. 20(*a*). Moreover, FIG. 20(*b*) is made on a plane including the optical path P1, and crossing the container 10 and the DUT 1. Though a case in which n1<n2a and n1<n2b is shown, the ninth embodiment may be applied to other cases (refer to FIGS. 12(b), 18(a) and 18(b)).

The DUT 1 according to the ninth embodiment is the same as that according to the sixth embodiment, and hence a description thereof is omitted.

Referring to FIG. 20(a), according to the contour in the front cross section of the DUT 1, the radii of the plane cross sections of the first cover portion 13a, the second cover portion 13b, the first concave portion 11a and the second concave portion 11b change along the height thereof. Thus, the contours of the front cross sections of the first cover portion 13a, the second cover portion 13b, the first concave portion 11a, and the second concave portion 11b are also formed as a result of a combination of a convex surface, a concave surface and a convex surface arranged from the top.

It should be noted that the optical paths P1 to P5 are the same as those of the sixth embodiment. Moreover, the first cover portion 13a and the second cover portion 13b are different from each other in shape.

With the container 10 according to the ninth embodiment, since the contours of the front cross sections of the first cover portion 13a and the second cover portion 13b are formed by the curved surfaces according to the change of the DUT 1 in the shape in the vertical direction, the optical path P5 can be situated on the extension of the optical path P1.

Tenth Embodiment

A tenth embodiment is a method for scanning the DUT 1 in the horizontal direction (X direction) using the containers 10 according to the first to ninth embodiments.

The configurations of the container 10 and the terahertz wave measurement device according to the tenth embodiment are the same as those according to the first to ninth embodiments, and hence a description thereof is omitted.

A description will now be given of an operation of the tenth embodiment. FIGS. 13(a) and 13(b) are plan views of the container 10 and the terahertz wave measurement device for describing the operation of the tenth embodiment. It should be noted that the container 10 according to the first embodiment is shown in FIGS. 13(a) and 13(b). However, with the containers 10 according to the second to ninth embodiments, the scanning method according to the tenth embodiment can be carried out. Scanning methods according to eleventh to fourteenth embodiments may similarly be carried out using the container 10 according to the first embodiment and the containers 10 according to the second to ninth embodiments.

Referring to FIG. 13(a), the terahertz wave output device 2 of the terahertz wave measurement device outputs the terahertz wave (hereinafter referred to as "output step"). The output terahertz wave transmits through the enclosure portion 12 and the DUT 1 while traveling on the optical paths P1 to P5 as described in the first embodiment, and is detected by the terahertz wave detector 4 of the terahertz wave measurement device (hereinafter referred to as "detection step"). As a result, the DUT 1 is measured by the terahertz wave measurement device.

During the output step and the detection step, the container 10 and the DUT 1 move horizontally (downward in FIGS. 13(a) and 13(b)) with respect to the optical paths P1 and P5 of the terahertz wave. As a result, the optical paths P1 and P5 intersect with a certain portion of the DUT 1 (which is different from that in FIG. 13(a)) as shown in FIG. 13(b).

According to the tenth embodiment, the DUT 1 can be scanned in the horizontal direction (X direction). As a result, the DUT 1 can be tomographically measured.

During the output step and the detection step, the same effect can be provided if the optical paths P1 and P5 of the terahertz wave move horizontally with respect to the container 10 and the DUT 1 (upward in FIGS. 13(a) and 13(b)). In order to move the optical paths P1 and P5 of the terahertz wave, the terahertz wave output device 2 and the terahertz wave detector 4 may be moved.

Eleventh Embodiment

The eleventh embodiment is a method for scanning the DUT 1 using the containers 10 according to the first to ninth embodiments while the DUT 1 is rotating.

The configurations of the container 10 and the terahertz wave measurement device according to the eleventh embodiment are the same as those according to the first to ninth embodiments, and hence a description thereof is omitted.

A description will now be given of an operation of the eleventh embodiment. FIGS. 14(a) and 14(b) are plan views of the container 10 and the terahertz wave measurement device for describing the operation of the eleventh embodiment. It should be noted that the definitions of the output step, the detection step, and the optical paths P1 and P5 are the same as those of the tenth embodiment.

Referring to FIG. 14(a), the output step is carried out. The output terahertz wave transmits through the enclosure portion 12 and the DUT 1 while traveling on the optical paths P1 to P5 as described according to the first embodiment. Then, the detection step is carried out. As a result, a certain part of the DUT 1 is measured by the terahertz wave measurement device.

While the output step and the detection step are carried out, the DUT 1 rotates about a line A extending vertically (Z direction) (refer to FIGS. 16(a), 16(b), 17(a) and 17(b)) as an axis of rotation (line A may not be a real object). For example, the DUT 1 rotates counterclockwise. Then, the DUT 1 is arranged as shown in FIG. 14(b). The part of the DUT 1 which intersects with the optical path P2 is different between the case in FIG. 14(b) and the case in FIG. 14(a). Thus, the case in FIG. 14(b) and the case in FIG. 14(a) can respectively measure different parts of the DUT 1.

According to the eleventh embodiment, the DUT 1 can be scanned while the DUT 1 is being rotated. As a result, the DUT 1 can be tomographically measured.

Twelfth Embodiment

The twelfth embodiment is a method for scanning the DUT 1 using the containers 10 according to the first to ninth embodiments while the container 10 and the optical paths P1 and P5 of the terahertz wave are rotated.

The configurations of the container 10 and the terahertz wave measurement device according to the twelfth embodiment are the same as those according to the first to ninth embodiments, and hence a description thereof is omitted.

A description will now be given of an operation of the twelfth embodiment. FIGS. 15(a) and 15(b) are plan views of the container 10 and the terahertz wave measurement device for describing the operation of the twelfth embodiment. It should be noted that the definitions of the output step, the detection step, and the optical paths P1 and P5 are the same as those of the tenth embodiment.

Referring to FIG. 15(a), the output step is carried out. The output terahertz wave transmits through the enclosure portion 12 and the DUT 1 while traveling on the optical paths P1 to P5 as described according to the first embodiment. Then, the detection step is carried out. As a result, a certain part of the DUT 1 is measured by the terahertz wave measurement device.

While the output step and the detection step are carried out, the container 10 and the optical paths P1 and P5 of the terahertz wave rotate about the line A extending vertically (Z direction) (refer to FIGS. 16(a), 16(b), 17(a) and 17(b)) as an axis of rotation. For example, they may rotate counterclockwise. Then, the DUT 1 is arranged as shown in FIG. 15(b). The part of the DUT 1 which intersects with the optical path P5 is different between the case in FIG. 15(b) and the case in FIG. 15(a). Thus, the case in FIG. 15(b) and the case in FIG. 15(a) can respectively measure different parts of the DUT 1.

According to the twelfth embodiment, the DUT 1 can be scanned while the container 10 and the optical paths P1 and P5 of the terahertz wave are rotating. As a result, the DUT 1 can be tomographically measured.

Thirteenth Embodiment

The thirteenth embodiment is a method for scanning the DUT 1 in the vertical direction (Z direction) using the containers 10 according to the first to ninth embodiments.

FIGS. 16(a) and 16(b) are front views of the container 10 and the terahertz wave measurement device according to the thirteenth embodiment. Configurations of the container 10 and the terahertz wave measurement device according to the thirteenth embodiment are approximately the same as those according to the first to ninth embodiments. However, the DUT 1 is cylindrical, and a part of the DUT 1 is stored in the gap portion 11 of the container 10.

A description will now be given of an operation of the thirteenth embodiment. It should be noted that the definitions of the output step, the detection step, and the optical paths P1 and P5 are the same as those of the tenth embodiment.

Referring to FIG. 16(a), the output step is carried out. The output terahertz wave transmits through the enclosure portion 12 and the DUT 1 while traveling on the optical paths P1 to P5 as described according to the first embodiment. Then, the detection step is carried out. As a result, a lower part of the DUT 1 is measured by the terahertz wave measurement device.

During the output step and the detection step, the container 10 and the optical paths P1 and P5 of the terahertz wave move vertically (upward in FIGS. 16(a) and 16(b)) with respect to the DUT 1. Then, the optical path P5 intersects with an upper part of the DUT 1 as shown in FIG. 16(b). As a result, the upper part of the DUT 1 is measured by the terahertz wave measurement device. It should be noted that, in order to move the optical paths P1 and P5 of the terahertz wave, the terahertz wave output device 2 and the terahertz wave detector 4 may be moved.

According to the thirteenth embodiment, the DUT 1 can be scanned in the vertical direction (Z direction). As a result, the DUT 1 can be tomographically measured.

During the output step and the detection step, the DUT 1 may move vertically with respect to the container 10 and the optical paths P1 and P5 of the terahertz wave.

Fourteenth Embodiment

The fourteenth embodiment is a method for scanning the DUT 1 in the vertical direction (Z direction) using the containers 10 according to the first to ninth embodiments.

FIGS. 17(a) and 17(b) are front views of the container 10 and the terahertz wave measurement device according to the fourteenth embodiment. It should be noted that only the DUT 1 is shown in a cross sectional view. Configurations of the container 10 and the terahertz wave measurement device according to the fourteenth embodiment are approximately the same as those according to the first to ninth embodiments. However, the DUT 1 is cylindrical, and the entirety of the DUT 1 is stored in the gap portion 11 of the container 10.

A description will now be given of an operation of the fourteenth embodiment. It should be noted that the definitions of the output step, the detection step, and the optical paths P1 and P5 are the same as those of the tenth embodiment.

Referring to FIG. 17(a), the output step is carried out. The output terahertz wave transmits through the enclosure portion 12 and the DUT 1 while traveling on the optical paths P1 to P5 as described according to the first embodiment. Then, the detection step is carried out. As a result, a lower part of the DUT 1 is measured by the terahertz wave measurement device.

During the output step and the detection step, the container 10 and the DUT 1 move vertically (downward in FIGS. 17(a) and 17(b)) with respect to the optical paths P1 and P5 of the terahertz wave. Then, the optical path P5 intersects with an upper part of the DUT 1 as shown in FIG. 17(b). As a result, the upper part of the DUT 1 is measured by the terahertz wave measurement device.

According to the fourteenth embodiment, the DUT 1 can be scanned in the vertical direction (Z direction). As a result, the DUT 1 can be tomographically measured.

During the output step and the detection step, the optical paths P1 and P5 of the terahertz wave may move vertically with respect to the container 10 and the DUT 1.

The invention claimed is:

1. A container for containing at least a part of a device under test to be measured by an electromagnetic wave measurement device, comprising:
    a gap portion that has, internally disposed therein, at least a part of the device under test; and
    an enclosure portion that comprises a first curved surface portion and a second curved surface portion, and the gap portion is positioned between the first curved surface portion and the second curved surface portion, thereby enclosing the gap portion, wherein:
    the refractive index n2 of the enclosure portion is larger than the refractive index n1 of the device under test;
    both the first curved surface and the second curved surface are convex surfaces; and
    the electromagnetic wave measurement device outputs an electromagnetic wave at a frequency equal to or more than 0.01 terahertz [THz] and equal to or less than 100 teraherz [THx] toward the device under test,
    the container is positioned such that an optical axis of the first curved surface portion intersects, at an angle of more than 0 degree and less than 90 degree, with the traveling direction of the electromagnetic wave, which is output from the electromagnetic wave measurement device toward the device under test, and before the electromagnetic wave is incident on the first curved surface portion.

2. The container according to claim 1, wherein a contour of a plane shape of the gap portion includes an arc.

3. The container according to claim 2, wherein a radius of a contour of a plane cross section of the gap portion changes according to the height of the gap portion.

4. The container according to claim 1, wherein:
the enclosure portion can be divided along a separation surface; and
the separation surface intersects with the gap portion.

5. The container according to claim 1, comprising an insertion member that is inserted in a space between the device under test and the gap portion, wherein:
a contour of a plane shape of an integrated body of the device under test and the insertion member is concentric with a contour of a plane shape of the gap portion; and
a relationship of $n1-0.1 \leq n3 \leq n1+0.1$ holds where $n3$ is the refraction index of the insertion member, and $n1$ is the refraction index of the device under test.

6. The container according to claim 5, wherein a distance between the contour of the plane shape of the integrated body of the device under test and the insertion member and the contour of the plane shape of the gap portion is equal to or less than a quarter of the wavelength of the electromagnetic wave output from the electromagnetic wave measurement device toward the device under test.

7. The container according to claim 1, comprising a filling material which is filled in a space between the device under test and the gap portion, wherein a relationship of $n1-0.1 \leq n4 \leq n1+0.1$ is satisfied, where $n4$ is the refraction index of the filling material, and $n1$ is the refraction index of the device under test.

8. The container according to claim 1, wherein a distance between a contour of a plane shape of the device under test and the contour of the plane shape of the gap portion is equal to or less than a quarter of the wavelength of the electromagnetic wave output from the electromagnetic wave measurement device toward the device under test.

9. The container according to claim 1, wherein the first curved surface portion and the second curved surface portion are cylindrical surfaces.

10. The container according to claim 1, wherein both of or either of the first curved surface portion and the second curved surface portion is a non-cylindrical surface.

11. A container arrangement method for arranging a container containing at least a part of a device under test to be measured by an electromagnetic wave measurement device, the container including:
a gap portion that has, internally disposed therein, at least the part of the device under test; and
an enclosure portion that comprises a first curved surface portion and a second curved surface portion, and the gap portion is positioned between the first curved surface portion and the second curved surface portion, thereby enclosing the gap portion, wherein:
the refractive index $n2$ of the enclosure portion is larger than the refractive index $n1$ of the device under test;
both the first curved surface and the second curved surface are convex surfaces; and
the electromagnetic wave measurement device outputs an electromagnetic wave at a frequency equal to or more than 0.01 teraherz [THz] and equal to or less than 100 teraherz [THz] toward the device under test,
the container arrangement method comprising:
arranging the container such that an optical axis of the first curved surface portion intersects, at an angle of more than 0 degree and less than 90 degree, with the traveling direction of the electromagnetic wave, which is output from the electromagnetic wave measurement device toward the device under test, and before the electromagnetic wave is incident on the first curved surface portion.

* * * * *